US009645212B2

(12) United States Patent
Frank et al.

(10) Patent No.: US 9,645,212 B2
(45) Date of Patent: May 9, 2017

(54) FIBER TRACTOGRAPHY USING ENTROPY SPECTRUM PATHWAYS

(71) Applicant: The Regents of the University of California, Oakland, CA (US)

(72) Inventors: Lawrence R. Frank, San Diego, CA (US); Vitaly L. Galinsky, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 19 days.

(21) Appl. No.: 14/919,605

(22) Filed: Oct. 21, 2015

(65) Prior Publication Data
US 2016/0110911 A1  Apr. 21, 2016

Related U.S. Application Data

(60) Provisional application No. 62/066,780, filed on Oct. 21, 2014.

(51) Int. Cl.
*G06K 9/00* (2006.01)
*G01R 33/48* (2006.01)
(Continued)

(52) U.S. Cl.
CPC ........ *G01R 33/4806* (2013.01); *A61B 5/0042* (2013.01); *A61B 5/055* (2013.01);
(Continued)

(58) Field of Classification Search
CPC ............ G01R 33/4806; G01R 33/5608; G01R 33/56341; A61B 5/055; A61B 5/00442; A61B 5/103; A61B 5/407; A61B 5/4064; A61B 5/4088; A61B 5/4561; A61B 5/7228; A61B 5/7264; A61B 5/7267; A61B 5/7278; A61B 5/742; A61B 6/027;
(Continued)

(56) References Cited

U.S. PATENT DOCUMENTS

| | | | |
|---|---|---|---|
| 6,992,484 B2 * | 1/2006 | Frank ............... | G01R 33/56341 324/307 |
| 7,672,790 B2 | 3/2010 | McGraw et al. | |

(Continued)

OTHER PUBLICATIONS

Behrens, T.E.J. et al., Probabilistic diffusion tractography with multiple fibre orientations: What can we gain?, NeuroImage vol. 34 (2007) pp. 144-155.
(Continued)

*Primary Examiner* — Jose Couso
(74) *Attorney, Agent, or Firm* — Eleanor Musick; Musick Davison LLP

(57) ABSTRACT

A method for fiber tractography processes multi-shell diffusion weighted MRI data to identify fiber tracts by calculating intravoxel diffusion characteristics from the MRI data. A transition probability is calculated for each possible path on the lattice, with the transition probability weighted according the intravoxel characteristics. Entropy is calculated for each path and the paths are ranked according to entropy. A geometrical optics algorithm is applied to the entropy data to define pathways, which are ranked according to their significance to generate a map of the pathways.

9 Claims, 21 Drawing Sheets
(12 of 21 Drawing Sheet(s) Filed in Color)

(51) Int. Cl.
| | | |
|---|---|---|
| *A61B 5/055* | (2006.01) | |
| *A61B 5/00* | (2006.01) | |
| *G01R 33/563* | (2006.01) | |
| *G06T 7/00* | (2017.01) | |

(52) U.S. Cl.
CPC .......... *A61B 5/4064* (2013.01); *A61B 5/7278* (2013.01); *A61B 5/742* (2013.01); *G01R 33/56341* (2013.01); *G06T 7/0081* (2013.01); *G06T 7/0087* (2013.01); *A61B 2576/026* (2013.01); *G06T 2207/10088* (2013.01); *G06T 2207/30016* (2013.01)

(58) Field of Classification Search
CPC ....... A61B 8/00; A61B 8/0833; A61B 8/0866; A61B 8/0883; A61B 8/4254; A61B 8/461; A61B 8/466; A61B 8/467; A61B 8/523; A61B 8/5238; A61B 2576/00–2576/026; G06T 1/00; G06T 3/00; G06T 5/00; G06T 5/002; G06T 5/003; G06T 5/10; G06T 5/20; G06T 7/00; G06T 7/0012; G06T 7/0042; G06T 7/0065; G06T 7/0081; G06T 7/0085; G06T 7/0087; G06T 7/0091; G06T 7/406; G06T 7/60; G06T 7/602; G06T 11/00; G06T 11/003; G06T 11/005; G06T 15/00; G06T 15/08; G06T 15/20; G06T 15/205; G06T 17/00; G06T 17/10; G06T 17/30; G06T 19/00; G06T 2200/04; G06T 2200/08; G06T 2207/10028; G06T 2207/10088; G06T 2207/10092; G06T 2207/10096; G06T 2207/20021; G06T 2207/20084; G06T 2207/20172; G06T 2207/20182; G06T 2207/20192; G06T 2207/30004; G06T 2207/30012; G06T 2207/30016; G06T 2207/30024; G06T 2207/30028; G06T 2207/30032; G06T 2207/30172; G06T 2210/41; G06T 2211/00; G06T 2215/06; G06T 2219/00; G06T 2219/20; G06K 9/0051; G06K 9/00516; G06K 9/40; G06K 2209/05–2209/051; G06F 19/16; G06F 19/24; G01S 15/8977; G01S 15/8993; G01V 1/30

See application file for complete search history.

(56) References Cited

U.S. PATENT DOCUMENTS

| | | | |
|---|---|---|---|
| 7,773,074 | B2 | 8/2010 | Arenson et al. |
| 8,742,754 | B2 | 6/2014 | Hasan |
| 9,404,986 | B2* | 8/2016 | White ............. G01R 33/56341 |
| 2005/0119834 | A1 | 6/2005 | Kita et al. |
| 2005/0213809 | A1 | 9/2005 | Lees et al. |
| 2006/0259282 | A1* | 11/2006 | Failla ................ A61N 5/1031 703/2 |
| 2008/0091388 | A1* | 4/2008 | Failla ................ A61N 5/1031 703/2 |
| 2008/0287796 | A1 | 11/2008 | Kiraly et al. |
| 2011/0201935 | A1 | 8/2011 | Collet-Billon et al. |
| 2011/0255763 | A1 | 10/2011 | Bogoni et al. |
| 2016/0110911 | A1 | 4/2016 | Frank et al. |
| 2016/0210742 | A1* | 7/2016 | Weiss .................... B60R 25/00 |
| 2016/0225146 | A1* | 8/2016 | Frank .................... A61B 5/055 |

OTHER PUBLICATIONS

Bista, Sujal et al., Visualization of Brain Microstructure through Spherical Harmonics Illumination of High Fidelity Spatio-Angular Fields, IEEE Trans Vis Comput Graph, Dec. 2014; 20(12): pp. 2416-2525.

Burda, Z. et al., The various facets of random walk entropy, presented at the 22nd Marian Smoluchowski Symposium on Statistical Physics, Zakopane, Poland, Sep. 12-17, 2009, 40 pgs.

Campbell, Jennifer S.W., et al., Diffusion Imaging of White Matter Fibre Tracts, Thesis submitted to McGill Jniversity, Nov. 8, 2004, Montreal, Canada, copyright Jennifer Campbell, 2004, 183 pgs.

Chung, Moo K. et al., Encoding cortical surface by spherical harmonics, Statistica Sinica vol. 18 (2008), 1269-1291.

Descoteaux, Maxime et al., Deterministic and probabilistic Q-Ball tractography: from diffusion to sharp fiber distributions, No. 6273, Aug. 2007, Theme BIO, 36 pgs.

Enrvik, Aron, 3D visualization of weather radar data, Thesis project in computer graphics at Linkoping University, Linkoping, Jan. 2002, LITH-ISY-EX-3252-2002, 92 pgs.

Frank, Lawrence R., et al., Information pathways in a disordered lattice, Physical Review, E89, 032142 (2014), 11 pgs.

Galinsky, Vitaly L. et al., Automated segmentation and shape characterization of volumetric data, NeuroImage vol. 92 (2014) pp. 156-168.

Galinsky, Vitaly L. et al., Simultaneous multi-scale diffusion estimation and tractography guided by entropy spectrum pathways, IEEE Transactions on Medical Imaging, Dec. 2104, vol. 34, Issue 5, pp. 1177-1193.

Goncalves, Vitor, Interaction and visualization techniques for volumetric data of various scalar modalities: integration of visualization and interaction, Electronica E. Telecomunicacoes, vol. 5, No. 3, Jun. 2011, pp. 344-351.

Huang, Heng, et al., Functional analysis of cardiac MR images using SPHARM modeling, Proc. SPIE 5747, Medical Imaging 2005: Image Processing, May 5, 2005, 1384; doi:10.1117/12.595954, 8 pgs.

International Search Report / Written Opinion for PCT/US2014/055712, mailed Dec. 8, 2014, 15 pgs.

Le Bihan, Denis, Diffusion, confusion and functional MRI, NeuroImage, 2011, doi: 10.1016/j.neuroimage.2011.09.058, 6 pgs.

Lu, Meng, et al. Snake-based brain white matter fiber reconstruction, Bio-Medical Materials and Engineering vol. 24 (2014) pp. 2945-2953.

Mukherjee, P. et al., Diffusion tensor MR imaging and fiber tractography: technical considerations, AJNR Am J. Neuroradiol vol. 29, May 2009, pp. 843-852.

Mukherjee, P. et al., Diffusion tensor MR imaging and fiber tractography: theoretic underpinnings, AJNR Am J. Neuroradiol vol. 29, Apr. 2008, pp. 632-641.

Peters, J.F., et al., Classification of meteorological volumetric radar data using rough set methods, Pattern Recognition Letters, vol. 24 (2003) pp. 911-920.

Senjem, Matthew L., et al., Comparison of different methodological implementations of Voxel-based morphometry in neurodegenerative disease, Neuroimage vol. 26(2), Jun. 2005, pp. 600-608.

Shaw, Christopher D., et al., Real-time weather data on terrain, Proc. SPIE 4368, Visualization of Temporal and Spatial Data for Civilian and Defense Applications, Aug. 23, 2001, 8 pages.

Sinatra, Roberta, et al., Maximal-entropy random walks in complex networks with limited information, Physical Review vol. 83, 030103(R), 2011, 4 pages.

Styner, Martin, Statistical shape analysis of brain structures using SPHARM-PDM, Insight Journal, MICCAI 2006 Opensource Workshop, 7 pages.

Tournier, Jacques-Donald, et al., Diffusion tensor imaging and beyond, Magn Reson Med. vol. 65(6), Jun. 2011, pp. 1532-1556.

* cited by examiner

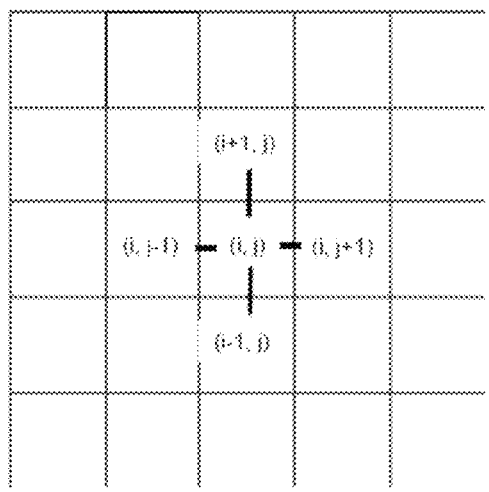
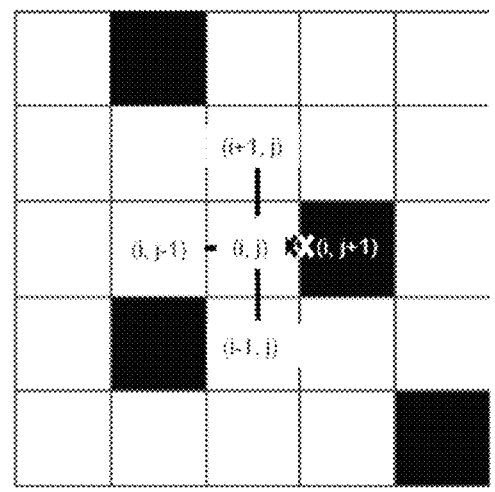
FIG. 2A
(prior art)
FIG. 2B
(prior art)
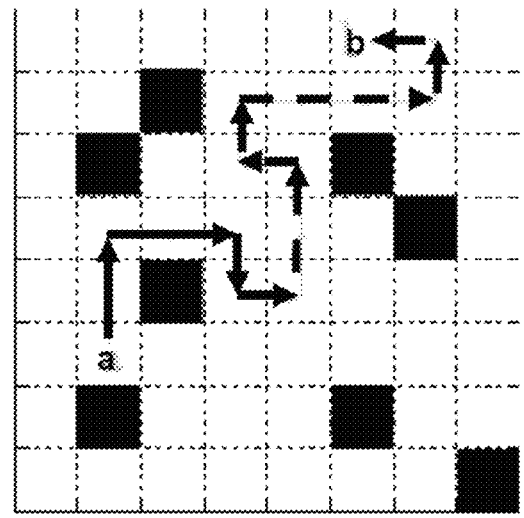
FIG. 3

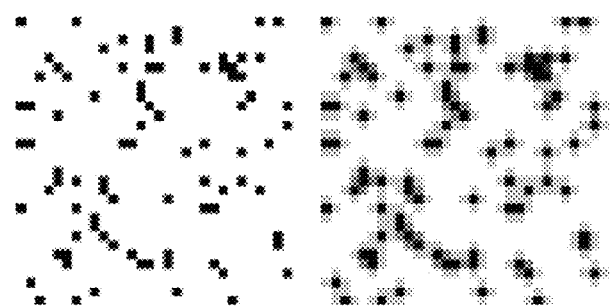
FIG. 6A  FIG. 6B
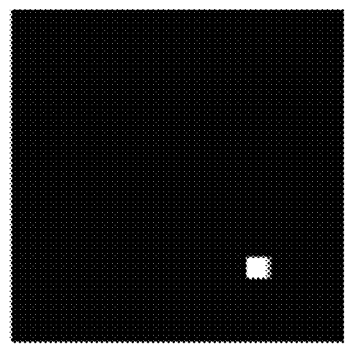 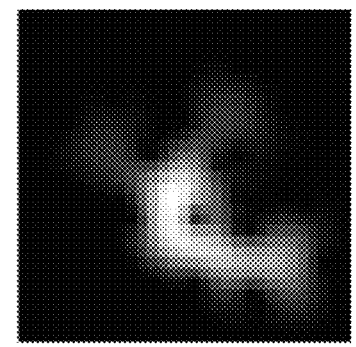
FIG. 6C  FIG. 6D
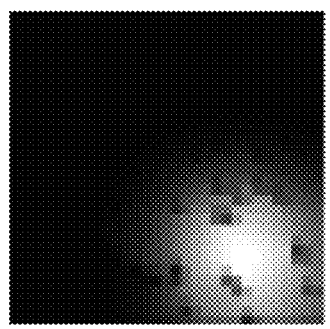 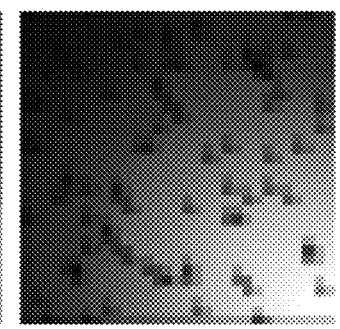
FIG. 6E  FIG. 6F
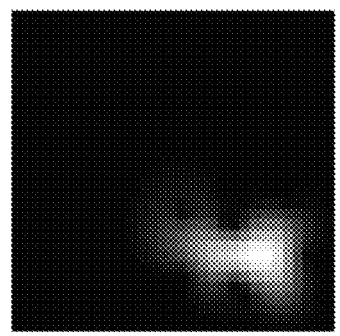 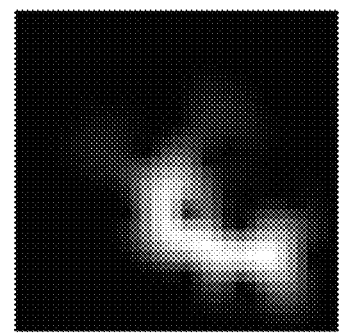
FIG. 6G  FIG. 6H

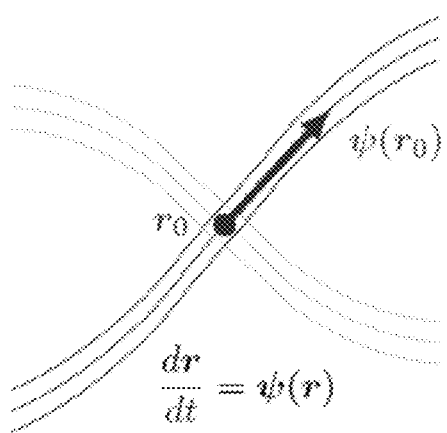 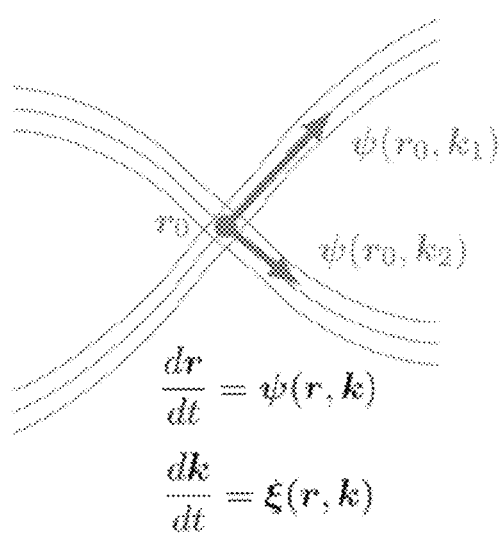
FIG. 12A  FIG. 12B

FIBER TRACTOGRAPHY USING ENTROPY SPECTRUM PATHWAYS

RELATED APPLICATIONS

This claims the benefit of the priority of Provisional Application No. 62/066,780, filed Oct. 21, 2014, which is incorporated herein by reference in its entirety.

GOVERNMENT RIGHTS

This invention was made with government support under Grant MH096100 awarded by the National Institutes of Health and Grant DBI-1147260 awarded by the National Science Foundation. The government has certain rights in the invention.

FIELD OF THE INVENTION

The present invention relates to a method for the characterization of connectivity within complex data and more particularly to a method for identifying neural pathways within DW-MRI data.

BACKGROUND

Magnetic Resonance Imaging (MRI), or nuclear magnetic resonance imaging, is commonly used to visualize detailed internal structures in the body. MRI provides superior contrast between the different soft tissues of the body when compared to x-ray computed tomography (CT). Unlike CT, MRI involves no ionizing radiation because it uses a powerful magnetic field to align protons, most commonly those of the hydrogen atoms of the water present in tissue. A radio frequency electromagnetic field is then briefly turned on, causing the protons to alter their alignment relative to the field. When this field is turned off the protons return to their original magnetization alignment. These alignment changes create signals that are detected by a scanner. Images can be created because the protons in different tissues return to their equilibrium state at different rates. By altering the parameters on the scanner this effect can be used to create contrast between different types of body tissue. MRI may be used to image every part of the body, and is particularly useful for neurological conditions, for disorders of the muscles and joints, for evaluating tumors, and for showing abnormalities in the heart and blood vessels. Magnetic resonance imaging (MRI) methods provide several tissue contrast mechanisms that can be used to assess the micro- and macrostructure of living tissue in both health and disease. Diffusion MRI is a method that produces in vivo images of biological tissues weighted with the local microstructural characteristics of water diffusion. There are two distinct forms of diffusion MRI, diffusion weighted MRI and diffusion tensor MRI. In diffusion weighted imaging (DWI), each image voxel (three-dimensional pixel) has an image intensity that reflects a single best measurement of the rate of water diffusion at that location. This measurement is more sensitive to early changes such as occur after a stroke than more traditional MRI measurements such as T1 or T2 relaxation rates. DWI is most applicable when the tissue of interest is dominated by isotropic water movement, e.g., grey matter in the cerebral cortex and major brain nuclei—where the diffusion rate appears to be the same when measured along any axis. Traditionally, in diffusion-weighted imaging (DWI), three gradient-directions are applied, sufficient to estimate the trace of the diffusion tensor or 'average diffusivity', a putative measure of edema. Clinically, trace-weighted images have proven to be very useful to diagnose vascular strokes in the brain, by early detection (within a couple of minutes) of the hypoxic edema.

Diffusion tensor imaging (DTI) is a technique that enables the measurement of the restricted diffusion of water in tissue in order to produce neural tract images instead of using this data solely for the purpose of assigning contrast or colors to pixels in a cross sectional image. It also provides useful structural information about muscle—including heart muscle, as well as other tissues such as the prostate. DTI is important when a tissue—such as the neural axons of white matter in the brain or muscle fibers in the heart—has an internal fibrous structure analogous to the anisotropy of some crystals. Water tends to diffuse more rapidly in the direction aligned with the internal structure, and more slowly as it moves transverse to the preferred direction. This also means that the measured rate of diffusion will differ depending on the position of the observer. In DTI, each voxel can have one or more pairs of parameters: a rate of diffusion and a preferred direction of diffusion, described in terms of three dimensional space, for which that parameter is valid. The properties of each voxel of a single DTI image may be calculated by vector or tensor math from six or more different diffusion weighted acquisitions, each obtained with a different orientation of the diffusion sensitizing gradients. In some methods, hundreds of measurements—each making up a complete image—can be used to generate a single resulting calculated image data set. The higher information content of a DTI voxel makes it extremely sensitive to subtle pathology in the brain. In addition, the directional information can be exploited at a higher level of structure to select and follow neural tracts through the brain—a process called tractography.

Tractography is the only available tool for identifying and measuring pathways in the brain (neural tracts) non-invasively and in-vivo. By comparison with invasive techniques, tractography measurements are indirect, difficult to interpret quantitatively, and error-prone. However, their non-invasive nature and ease of measurement mean that tractography studies can address scientific questions that cannot be answered by any other means. In particular, brain connections can be measured in living human subjects, and measurements can be made simultaneously across the entire brain. Hence, areal connections may be compared in humans across many cortical and sub-cortical sites. Furthermore, connections can be compared with other in-vivo measures such as functional connectivity and behavior across individuals.

More extended diffusion tensor imaging (DTI) scans derive neural tract directional information from the data using 3D or multidimensional vector algorithms based on three, six, or more gradient directions, sufficient to compute the diffusion tensor. The diffusion model is a rather simple model of the diffusion process, assuming homogeneity and linearity of the diffusion within each image voxel. From the diffusion tensor, diffusion anisotropy measures such as the fractional anisotropy (FA) can be computed. The principal direction of the diffusion tensor can be used to infer the white-matter connectivity of the brain. Recently, more advanced models of the diffusion process have been proposed to overcome the weaknesses of the diffusion tensor model. Amongst others, these include q-space imaging and generalized diffusion tensor imaging.

Reconstruction of tissue fiber pathways from volumetric diffusion weighted magnetic resonance imaging (DW-MRI) data is an inherently ill-posed problem because the local (voxel) diffusion measurements are noisy and made on a scale significantly greater than the underlying fibers and, thus, there are a multitude of possible neural pathways between any two given points in the imaging volume that might be consistent with the experimental data. The question then is to find the paths that are most probable. Current fiber tractography methods generally fall into two categories: 1) deterministic methods, typically based on some form of streamline construction, probabilistic methods, also generally based on streamline construction, but with the most likely principal diffusion direction determined from a posterior distribution of principal diffusion directions. These algorithms are "local" in the sense that the computations are done at each voxel and some small neighborhood around it and thus are not informed by the final path that is created, and thus are not capable of assessing the probability of the final path amongst all possible paths. In most cases, these algorithms are inherently based upon some underlying relation to a random walk which guides the evolution of the trajectories.

Recently, interest has grown in more "global" methods that take into account the probabilities of the final paths by incorporating the path probabilities into the estimation process. These methods are typically based upon parameterizations of the diffusion field, or the anatomical connections they imply, that extend spatially beyond the voxel dimensions and subsequently take the form of either improving the local computations by the incorporation of more spatially extended path lengths or on the extremization of a cost function over a multitude of possible paths. These global methods usually (with some exceptions do not take the random walk viewpoint but rather view the entire system as possessing some underlying structure, characterized by local interactions or potentials, that can be elucidated by optimizing some cost function (e.g., energy) over multiple configurations of that system.

The original diffusion tensor imaging (DTI) model assumes that the measurements in each voxel provide an estimate of a single real, 3×3 symmetric diffusion tensor D from whose eigenstructure can be derived both a meaningful measure of the anisotropy (here characterized by the fractional anisotropy FA and a principal eigenvector that can be used as a proxy for the fiber orientation. Then DTI is the simplest underlying model for diffusion tensor data, is predicated on a single fiber model for the voxel content, and is equivalent to a Gaussian model for diffusion. However, the DTI model is not sufficient to capture more realistic possibilities of complex fiber crossings needed for clinical applications. To estimate local diffusion directions in each voxel (streamline directions) several high angular resolution diffusion imaging (HARDI) methods are typically used. These methods represent an extension of the original DTI method to higher angular resolutions appropriate not only for detection of main fiber orientation, but also for attempting to resolve more complex intravoxel fiber architecture such as multiple crossing fibers.

In recent years, there has been significant interest in developing DW-MRI methods capable not only of estimating angular fiber distributions from multidirectional diffusion imaging (multiple q-angles), but also find spatial scales with multiple diffusion weightings (multiple b-shells). While it has long been recognized that the most general nonparametric (model-free) approach is to measure the displacement probability density function or diffusion propagator directly, the natural extension of this to imaging wherein 3D Cartesian sampling of q-space is used to obtain the 3D displacement probability density function (dPDF) at each voxel, is prohibitively expensive from the standpoint of data acquisition. This recognition has recently spawned more practical methods for obtaining an estimate of the dPDF, often called the ensemble average propagator (EAP), from more practical multi-shell, multi-directional acquisitions. See, e.g., Merlet, et al., "TRactography via the Ensemble Average Propagator in diffusion MRI"

Despite these advances, a critical simplification that is made in all current methods used to estimate either the intravoxel diffusion characteristics (via the EAP, for example) or to estimate the underlying global structure (tractography) is the assumption that these two estimation procedures are independent. Thus, one must first estimate the intravoxel diffusion, then apply a tractography algorithm. For example, multiple b-shell effects, used in obtaining the EAP, are used only to infer directional multiple fiber information for input into streamline tractography algorithms. However, this distinction between local and global estimation is artificial and limiting, since both the local (voxel EAP) information and the global structure (tracts) are from the same tissue, just seen at different scales.

BRIEF SUMMARY

In an embodiment of the invention, a method and system are provided for characterization of connectivity within complex data. The inventive method may be used for a wide range of applications in which connectivity needs to be inferred from complex multi-dimensional data, such as magnetic resonance imaging (MRI) of the human brain using diffusion tensor magnetic resonance imaging (DT-MRI) for characterization of neuronal fibers and brain connectivity, or in the analysis of networks in the human brain using functional MRI (fMRI).

Characterization of connectivity with data is a complex procedure that is often approached with ad-hoc methods. The inventive method provides a solution to the problem of assessing global connectivity within complex data sets. The method, referred to as "Entropy Spectrum Pathways", or "ESP", is based on the description of pathways according to their entropy, and provides a method for ranking the significance of the pathways. The method is a generalization of the maximum entropy random walk ("MERW"), which appears in the literature as a description of a diffusion process that possesses localization of probabilities. The inventive approach expands the use of MERW beyond diffusion, and applies it as a measure of information. Additional applications include network analysis.

A computer-implemented method for fiber tractography based on Entropy Spectrum Pathways includes instructions fixed in a computer-readable medium that cause a computer processor to solve an eigenvector problem for the probability distribution and use it for an integration of the probability conservation through ray tracing of the convective modes guided by a global structure of the entropy spectrum coupled with a small scale local diffusion. The intervoxel diffusion is sampled by multi b-shell multi q-angle DWI data expanded in spherical harmonics and spherical Bessel series.

In some embodiments, a method for fiber tractography processes multi-shell diffusion weighted MRI data to identify fiber tracts by calculating intravoxel diffusion characteristics from the MRI data. A transition probability is calculated for each possible path on the lattice, with the transition probability weighted according the intravoxel characteristics. Entropy is calculated for each path and the paths are ranked according to entropy. A geometrical optics algorithm is applied to the entropy data to define pathways, which are ranked according to their significance to generate a map of the pathways.

In one aspect, the inventive method includes acquiring, via an imaging system, diffusion weighted MRI data comprising a plurality of voxels, wherein the plurality of voxels defines a lattice, each voxel connected by a path; inputting the MRI data into a computer processor data having instructions stored therein for causing the computer processor to execute the steps of: calculating intravoxel diffusion characteristics from the MRI data; calculating a transition probability for each path on the lattice, wherein the transition probability is weighted according the intravoxel characteristics; calculating an entropy for each path; ranking the paths between two voxels according to entropy to determine a maximum entropy; calculating a connection between a global structure of the probability with a local structure of the lattice by applying the Fokker-Planck equation to one or more highest ranked paths, wherein potential equals entropy; calculating a location and direction of one or more fiber tracts by applying geometric optics algorithms to the results of the Fokker-Planck equation; and generating an output comprising a display corresponding to the one or more fiber tracts. In an embodiment of the method, the Fokker-Planck equation is $\partial_t P + \nabla \cdot (L P \nabla S) = \nabla \cdot D \nabla P$, where P is the probability, S is the entropy, and L is a local diffusion tensor, where $L = \kappa D$, where $\kappa$ is the Onsager coefficient. In another embodiment, the geometric optics algorithms comprise $$\frac{dr}{dt} = \frac{2}{V_R} \int [X(k \cdot X) + 2kY|k|^2 - Z]dR$$

and $$\frac{dk}{dt} = -\frac{2}{V_R} \int [(k \cdot X)\nabla(k \cdot X) + (|k|^2 Y - Z)(|k|^2 \nabla Y - \nabla Z)]dR,$$

where r is the location, R is displacement, k is the direction, t is time, $X = \nabla P_0(2 + \ln P_0) + \nabla(P_0(1 + \ln P_0))$, $Y = P_0(1 + \ln P_0)$, and $Z = \nabla \cdot \nabla P_0(2 + \ln P_0)$.

In another aspect of the invention, a method for fiber tractography comprises acquiring, via an imaging system, diffusion weighted MRI data comprising a plurality of voxels, wherein the plurality of voxels defines a lattice, each voxel connected by a path; inputting the MRI data into a computer processor data having instructions stored therein for causing the computer processor to execute the steps of: calculating intravoxel diffusion characteristics from the MRI data; calculating a transition probability for each path on the lattice, wherein the transition probability is weighted according the intravoxel characteristics; calculating an entropy for each path; ranking the paths between two voxels according to entropy to determine a maximum entropy; calculating a connection between a global structure of the probability with a local structure of the lattice for one or more highest ranked paths; determining one or more fiber tracts corresponding to the highest ranked paths using ray tracing, wherein potential equals entropy; and generating an output comprising a display corresponding to the one or more fiber tracts. In one embodiment, calculating a connection comprises applying the relationship $\partial_t P + \nabla \cdot (L P \nabla S) = \nabla \cdot D \nabla P$ to the one or more highest ranked paths, where P is probability=$P_0 + P_1$, S is the entropy, D is a diffusion coefficient, and L is a local diffusion tensor, where $L = \kappa D$, where $\kappa$ is the Onsager coefficient. In another embodiment, ray tracing comprises applying geometric optics algorithms to the highest ranked paths according to the relationships $$\frac{dr}{dt} = \frac{2}{V_R} \int [X(k \cdot X) + 2kY|k|^2 - Z]dR$$

and $$\frac{dk}{dt} = -\frac{2}{V_R} \int [(k \cdot X)\nabla(k \cdot X) + (|k|^2 Y - Z)(|k|^2 \nabla Y - \nabla Z)]dR,$$

where r is the location, R is the displacement, k is the direction, t is time, $X = \nabla P_0(2 + \ln P_0) + \nabla(P_0(1 + \ln P_0))$, $Y = P_0(1 + \ln P_0)$, and $Z = \nabla \cdot \nabla P_0(2 + \ln P_0)$.

In still another aspect of the invention, a method for fiber tractography comprises acquiring, via an imaging system, multi-shell diffusion weighted MRI data comprising a plurality of voxels, wherein the plurality of voxels define locations on a lattice, each location connected by a path; and in a computing device, executing the steps of: performing a spherical wave decomposition on the data to define a set of spherical wave decomposition coefficients; using the spherical wave decomposition coefficients, generating a coupling matrix for diffusion connectivity at multiple scales, wherein the coupling matrix defines interactions between locations on the lattice; using the coupling matrix, computing transition probabilities and equilibrium probabilities for a plurality of interactions between locations on the lattice; using the computed transition probabilities to represent angular and scale distributions of potential paths between locations on the lattice; applying a geometric optics tractography algorithm to the transition probabilities to construct possible pathways, each possible pathway having an eigenvector and an eigenvalue; calculating eigenmodes for the possible pathways; ranking the possible pathways according to their eigenmode; defining a preselected number of pathways from the ranked pathways; and displaying the preselected number of pathways on a visual display.

Applications of the ESP method include any commercial neuroscience application involved in the quantification of connectivity, including neural fiber connectivity using diffusion tensor imaging, functional connectivity using functional MRI, or anatomical connectivity using segmentation analysis. The ESP method may also be used as a tool for characterization of connectivity in networks, examples of which include the internet and communications systems.

The present invention provides a method for the simultaneous estimation of local diffusion and global fiber tracts. The ESP method can be further enhanced by introducing a new approach to include multi-scale and multi-modal diffusion field into a scalar information entropy flow.

For the first time in neuroscience, the ESP method provides for the application of probability conservation to obtain fiber tracts through ray tracing of the convective modes guided by a global structure of the entropy spectrum coupled with small scale local diffusion. The method uses a novel approach to incorporate global information about multiple fiber crossings in each individual voxel and rank it in a scientifically rigorous manner. The method exploits six dimensional space for tracking neurofibers, providing a significant improvement over the three-dimensional positional tracking methods currently in use. The method avoids the need for an expensive front evolution step, which is common in the majority of current approaches. Instead, it is able to derive more complete and accurate path information more efficiently from the global entropy spectrum.

BRIEF DESCRIPTION OF THE DRAWINGS

This application includes at least one drawing executed in color. Copies of this application with color drawing(s) will be provided by the Patent and Trademark Office upon request and payment of the necessary fee.

FIGS. 2A and 2B illustrate random walks on a two-dimensional lattice, where FIG. 2A shows a regular lattice and FIG. 2B shows a defective lattice.

FIG. 3 illustrates a path on a defective lattice found by splitting the path into segments.

FIGS. 6A-6H illustrate the dynamic evolution of the generic random walk (GRW) and the maximum entropy random walk (MERW) for the lattice with $\rho=0.1$ of FIG. 6A; FIG. 6B shows the degrees of the lattice of FIG. 6A; FIG. 6C shows a point distribution of the lattice; FIG. 6D shows the transition probability; FIGS. 6E-6F show the GRW at t=50 and 300, respectively, and FIGS. 6G-6H show the MERW at t=50 and 300, respectively, for the lattice of FIG. 6A with a starting distribution shown in FIG. 6C. The lattice "defects" are inaccessible regions.

FIGS. 12A and 12B are schematic illustrations of a traditional fiber tracking based on integration of a single Frenet equation versus a fiber tracking according to an embodiment of the invention using the geometrical optics analogy, respectively.

FIGS. 18A-18D correspond to different projections and FIGS. 18E and 18F show tracts with seeds in corpus callosum and fasciculus respectively.

DETAILED DESCRIPTION OF EXEMPLARY EMBODIMENTS

Figure 1:
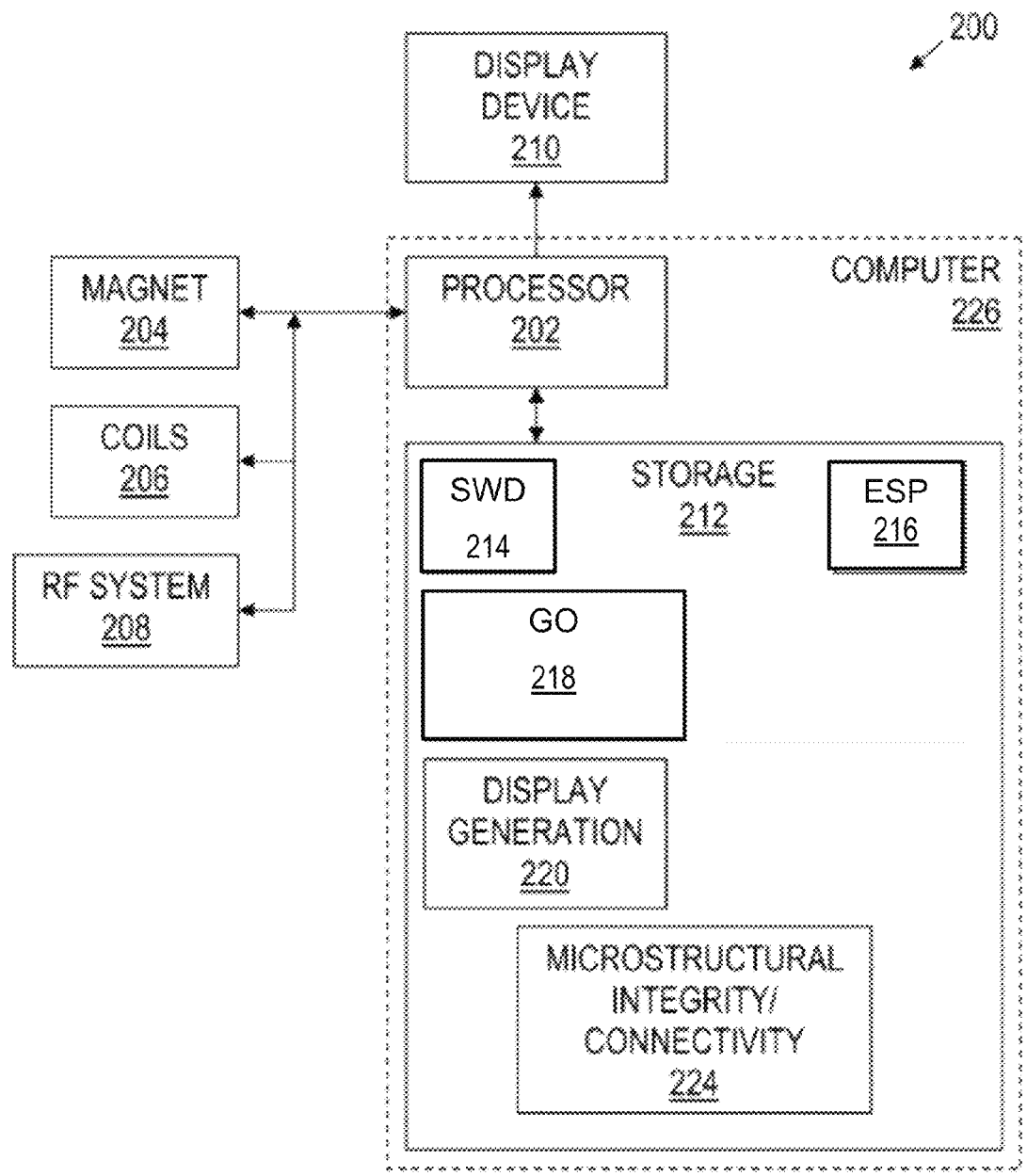
FIG. 1 is a block diagram of an exemplary imaging system in accordance with various embodiments.

FIG. 1 shows a block diagram of an exemplary magnetic resonance (MR) imaging system 200 in accordance with various embodiments. The system 200 includes a main magnet 204 to polarize the sample/subject/patient; shim coils 206 for correcting inhomogeneities in the main magnetic field; gradient coils 206 to localize the MR signal; a radio frequency (RF) system 208 which excites the sample/subject/patient and detects the resulting MR signal; and one or more computers 226 to control the aforementioned system components.

A computer 226 of the imaging system 200 comprises a processor 202 and storage 212. Suitable processors include, for example, general-purpose processors, digital signal processors, and microcontrollers. Processor architectures generally include execution units (e.g., fixed point, floating point, integer, etc.), storage (e.g., registers, memory, etc.), instruction decoding, peripherals (e.g., interrupt controllers, timers, direct memory access controllers, etc.), input/output systems (e.g., serial ports, parallel ports, etc.) and various other components and sub-systems. The storage 212 includes a computer-readable storage medium.

Software programming executable by the processor 202 may be stored in the storage 212. More specifically, the storage 212 contains software instructions that, when executed by the processor 202, causes the processor 202 to acquire multi-shell diffusion weighted magnetic resonance (MRI) data in the region of interest ("ROI") and process it using a spherical wave decomposition (SWD) module (SWD module 214); compute entropy spectrum pathways (ESP) (ESP module 216); perform ray tracing using a geometric optics tractography algorithm (GO module 218) to generate graphical images of fiber tracts for display (e.g., on display device 210, which may be any device suitable for displaying graphic data) the microstructural integrity and/or connectivity of ROI based on the computed MD and FA (microstructural integrity/connectivity module 224). More particularly, the software instructions stored in the storage 212 cause the processor 202 to display the microstructural integrity and/or connectivity of ROI based on the SWD, ESP and GO computations.

Additionally, the software instructions stored in the storage 212 may cause the processor 202 to perform various other operations described herein. In some cases, one or more of the modules may be executed using a second computer of the imaging system. (Even if the second computer is not originally or initially part of the imaging system 200, it is considered in the context of this disclosure as part of the imaging system 200.) In this disclosure, the computers of the imaging system 200 are interconnected and are capable of communicating with one another and performing tasks in an integrated manner. For example, each computer is able to access the other's storage.

In other cases, a computer system (similar to the computer 226), whether being a part of the imaging system 200 or not, is used for post-processing of diffusion MRI data that have been acquired. In this disclosure, such a computer system comprise one or more computers and the computers are interconnected and are capable of communicating with one another and performing tasks in an integrated manner. For example, each computer is able to access another's storage. Such a computer system comprises a processor and a computer-readable storage medium (CRSM). The CRSM contains software that, when executed by the processor, causes the processor to obtain diffusion magnetic resonance (MRI) data in region of interest (ROI) in a patient and process the data by performing spherical wave decomposition (SWD), entropy spectrum pathway (ESP) analysis and applying geometric optics algorithms to execute ray tracing operations to define fiber tracts for display on a display device.

The inventive method provides a solution to the problem of assessing global connectivity within complex data sets. The method, referred to as "Entropy Spectrum Pathways", or "ESP", described below, is based on the description of pathways according to their entropy, and provides a method for ranking the significance of the pathways. The method is a generalization of the maximum entropy random walk ("MERW"), which appears in the literature as a description of a diffusion process that possesses localization of probabilities. The inventive approach expands the use of MERW beyond diffusion, and applies it as a measure of information. Additional applications include network analysis.

Entropy Spectrum Pathways (ESP):

According to the ESP method, the MERW solution can be viewed as a specific manifestation of a more general result concerning inference on a lattice which has nothing necessarily to do with diffusion, or any other physical process. The general approach results in a new theoretical framework suitable for application to a wide range of problems involved with analysis of disordered lattice systems. As a byproduct, we show that the previous interpretation of the localization phenomenon by the Lifshitz sphere argument is not true in general. Moreover, the correct general solution we derive elucidates the source of the localization phenomenon, demonstrates that it actually occurs on multiple scales, and paves the way for the classification of optimal pathways of information in a lattice.

Consider the random walk on a two-dimensional lattice—a random walk is defined by the simple rule that at each time step a particle at location (i, j) can move one step in either the i or j direction. In a standard, or generic, random walk (GRW), all lattice sites are accessible, as illustrated in FIG. 2A. In a defective lattice, certain sites are inaccessible, as shown in FIG. 2B, in which the white squares are allowed and black squares ("the defects") are not.

Consider a 2D Cartesian grid of equally spaced points at R spatial locations $(x_1, \ldots, x_R)$ where each point can take on any one of s available values $\{v_1, \ldots, v_s\}$. To simplify the notation, we will equate the spatial path with the sequence of values and speak of the trajectory as the sequence of values along the spatial path: $\gamma_{ba}^n = \{v_{x_0}, v_{x_1}, \ldots, v_{x_n}\}$ and compute the probability of this sequence $p(\gamma_{ba}^n | I) = p(v_{x_0}, v_{x_1}, \ldots, v_{x_n} | I)$ given our prior information I.

The logical procedure for determining the path probabilities is the principle of maximum entropy in which the Shannon information entropy $$S(\gamma) = -\sum_{\{\gamma\}} p(\gamma) \ln p(\gamma) \tag{1}$$

is maximized subject to the constraints imposed by the basic rules of probability theory and by the s data points $u_k$ for $k = 1, \ldots, s$:

$$p(\gamma) \geq 0, \tag{2a}$$

$$\sum_{\{\gamma\}} p(\gamma) = 1, \tag{2b}$$

$$\sum_{\{\gamma\}} p(\gamma) u_k(\gamma) = \{u_k\} \equiv u_k, \tag{2c}$$

where the $U_k$ are the expected values of the data along the set of all possible paths $\{\gamma\}$. This is a variational problem solved by the method of Lagrange multipliers and has the general solution:

$$p(\gamma) = Z^{-1} \exp[-\Lambda(\gamma)], \tag{3}$$

where $$\Lambda(\gamma) = \sum_{k=1}^{s} \lambda_k u_k(\gamma), \tag{4}$$

and the partition function is $$Z(\lambda_1, \ldots, \lambda_s) = \sum_{\{\gamma\}} \exp[-\Lambda(\gamma)]. \tag{5}$$

The Lagrange multipliers $\{\lambda_k\}$ are determined from the data by $$\langle u_k \rangle = -\frac{\partial}{\partial \lambda_k} \ln Z(\lambda_1 \ldots \lambda_s), \quad (6)$$

for k=1, . . . , s, and the fluctuations are determined from $$\langle u_k u_l \rangle - \langle u_k \rangle \langle u_l \rangle = -\frac{\partial^2}{\partial \lambda_k \partial \lambda_l} \ln Z(\lambda_1 \ldots \lambda_s). \quad (7)$$

The entropy Eq. 1 of the maximum entropy distribution Eq. 3 is $$S = \ln Z + \sum_k \lambda_k u_k. \quad (8)$$

The reformulation of the path probabilities in terms of the maximum entropy formalism, as expressed by Eqs. 3-8, allows the construction of path probabilities consistent with given prior information. We now consider two different sets of prior information and show how these lead to the GRW and MERW, respectively. We stress here the fact that the dependence of the derived distribution p(γ) on the prior information means that it is an expression of our processing of information, rather than of a physical effect. Moreover, while the specific examples described herein are confined to prior information about nearest neighbor coupling, the formalism is very general and can incorporate prior information about more complex couplings.

Suppose that the known values $v_i$ represent the node degrees d and that the prior information consists of the frequency $f_i$ with which each value $d_i$ occurs. If $N_i$=number of times $d_i$ appears along γ, and $f_i$=expected frequencies of $d_i$, then $$\langle N_i \rangle = \sum_{\{\gamma\}} N_i(\gamma) p(\gamma) = N f_i, \quad i = 1, \ldots, s \quad (9)$$

where N=$\Sigma_i$ $N_i$ is the total number of sites visited. The path probability p(γ) is then found by maximizing Eq. 1 subject to Eq. 2a, Eq. 2b, and Eq. 2c (in the form of Eq. 9). The solution is then:

$$p(\gamma) = \frac{1}{Z} \exp\left[-\sum_{i=1}^{s} \lambda_i N_i(\gamma)\right] \quad (10)$$

where the partition function is $$Z(\lambda_i) = \sum_{\{\gamma\}} \exp\left[-\sum_{i=1}^{s} \lambda_i N_i(\gamma)\right] = z^N \quad (11)$$

and $$z = \sum_{i=1}^{s} e^{-\lambda_i} \quad (12)$$

From Eq. 6 and Eq. 9

$$\lambda_i = -\ln(z f_i), 1 \leq i \leq s, \quad (13)$$

which, when substituted into Eq. 3 and properly normalized, gives the multinomial distribution $$p(\gamma) = \prod_{i}^{n} \frac{1}{d_{x_i}} = \prod_{j=1}^{s} \left(\frac{1}{d_j}\right)^{N_j} \quad (14)$$

For 2D Cartesian lattice s=4. The number of different paths for specified $N_i$ is $N!/(N_1! \ldots N_s!)$. Eq. 14 says that the probability of any path only depends on how many times the values $\{v_i\}$ appear along the path, but not on the order in which they appear. Thus the GRW can be viewed as the maximum entropy solution when the prior information is limited to the frequency of occurrences of the defects.

Supposing that the prior information consists of the frequency $f_{ij}$ with which the pairs of value $v_i v_j$ occur together. At the end, we will consider the special case in which this information is reduced to whether or not location i and j are connected, on that the prior information is just the adjacency matrix. Now we consider the more general case where $N_{ij}$=number of times $v_i v_j$ appears along γ, and $f_{ij}$=expected frequencies of the pairs $v_i v_j$, and the $f_{ij}$ are known (they are again the prior information), then $$\langle N_{ij} \rangle = \sum_{\{\gamma\}} N_{ij}(\gamma) p(\gamma) = (n-1) f_{ij}, \quad \{i, j\} = 1, \ldots, s, \quad (15)$$

where n=$\Sigma_{ij}$ $N_{ij}$ is the total number of jumps between sites, and thus the trajectory length, and again $\{\gamma\}$ denotes the set of all possible paths γ. In the path γ the number of times the pair $x_i x_j$ appears is $$N_{ij}(\gamma) = \sum_{k=1}^{n-1} \delta_{i,k} \delta_{j,k+1} \quad (16)$$

where δ represents the Dirac delta function: $\delta_{i,j}$=1 if i=j and $\delta_{i,j}$=0 for i≠j.

The problem is logically identical to the problem of diagram frequencies in communication theory addressed by Jaynes. The path probability p(rγ) that has maximum entropy subject to the constraint Eq. 15 has the solution $$p(\gamma) = \frac{1}{Z} \exp\left[-\sum_{i,j=1}^{s} \lambda_{ij} N_{ij}(\gamma)\right] \quad (17)$$

where the partition function is $$Z(\lambda_{ij}) = \sum_{\{\gamma\}} \exp\left[-\sum_{i,j=1}^{s} \lambda_{ij} N_{ij}(\gamma)\right] \quad (18)$$

This complicated sum over all the different paths γ is simplified by noting that this partition function can be rewritten in terms of a matrix product $$Z(\lambda_{ij}) = \sum_{i,j=1}^{s} [Q^{(n-1)}]_{ij} \qquad (19)$$

where the matrix Q is defined as $$Q_{ij} = e^{-\lambda_{ij}}$$

Thus, each transition probability is associated with a standard eigenvalue equation $$\sum_{j} Q_{ij} \psi_{j}^{(k)} = \lambda_k \psi_i^{(k)}. \qquad (20)$$

This matrix defines the interactions between locations on the lattice and so will be called the "coupling matrix." As we show later, the Lagrange multiplier $\lambda_{ij}$ that define the interactions can be seen as local potentials that depend on some function of the spatial locations on the lattice. We will suppress the more complete notation $\lambda_{ij}(x_{ij})$, and thus Q ($x_{ij}$), for clarity.

A useful trick to simplify the computation of the partition function is to add the step ($x_n$, $x_i$) to the pathway, which adds another exp($-\lambda_{ij}$) to the partition function Eq. 18 and creates periodic boundary conditions. This modifies Eq. 19 to $$Z(\lambda_{ij}) = \sum_{i,j=1}^{s} [Q^n]_{ij} = Tr(Q^n) = \sum_{k=1}^{s} q_k^n \qquad (21)$$

where $\{q_k\}$ are the roots of $|Q_{ij} - q\delta_{ij}|$. This trick is justified in the limit of long trajectories $n \to \infty$. The probability of the entire path, Eq. 17 can be written using Eq. 16 and Eq. 20

$$p(\gamma_{ab}|I) = Z^{-1} Q_{x_1,x_2} Q_{x_2,x_3} \ldots Q_{x_{n-1},x_n} \qquad (22)$$

where the periodic boundary conditions trick has been invoked.

While Eq. 17 is formally the solution of the path probability, we would like to determine the transition probability. In order to do this, we can consider the problem of how our estimates change as we move along a path. In other words, if we have moved part way along a path, what does this tell us about the remainder of the path? This is analogous to the partial message problem. To address this question, imagine that we break the path yab from an initial point a to a final point b into two segments (FIG. 3) defined by some intermediate point $c = x_{m-1}$ (i.e., $a \le c \le b$), so that the first segment of the path is of length m−1 and the second segment is of length n−m+1:

$$\gamma_{ac}^{(m-1)} = v_{x_1} v_{x_2} \ldots v_{x_{m-1}} \qquad (23a)$$

$$\gamma_{cb}^{(n-m+1)} = v_{x_m} v_{x_{m+1}} \ldots v_{x_n} \qquad (23b)$$

The probability of the entire path is just the joint probability of the two path segments $\{\gamma_{ac}, \gamma_{cb}\}$ and from the basic rules of probability theory is equal to Eq. 17:

$$p(\gamma_{ab}|I) = p(\gamma_{ab}\gamma_{cb}|I) = p(\gamma_{cb}|\gamma_{ac},I)p(\gamma_{ac}|I) \qquad (24)$$

so the conditional probability of $\gamma_{cb}$, given $\gamma_{ac}$, is $$p(\gamma_{cb}|\gamma_{ac}, I) = \frac{p(\gamma_{ac}\gamma_{cb}|I)}{p(\gamma_{ac}|I)} = \frac{p(\gamma_{ab}|I)}{p(\gamma_{ac}|I)} \qquad (25)$$

The marginal distribution of initial part of the path, $p(\gamma_{ac}|I)$, is $$p(\gamma_{ac}|I) = \sum_{\gamma_{bc}} p(\gamma_{ab}|I) = \sum_{x_m=1}^{s} \ldots \sum_{x_n=1}^{s} p(x_1 \ldots x_n|I) \qquad (26)$$

which, from Eq. 22, is $$p(\gamma_{ac}|I) = R \sum_{x_m=1}^{s} \ldots \sum_{x_n=1}^{s} Q_{x_{m-1},x_m} \ldots Q_{x_{n-1},x_n} \qquad (27)$$

where $$R = Z^{-1} Q_{x_1,x_2} \ldots Q_{x_{m-2},x_{m-1}} \qquad (28)$$

Define the transition point from the initial path as ij where $i = x_{m-1}$ is the last point in the first path and $j = x_m$ is the first point in the second path. Just as in the step from Eq. 18 to Eq. 19, the sum over paths in Eq. 27 can be written as a matrix product:

$$p(\gamma_{ac}|I) = R \sum_{k,l=1}^{s} Q_{ik} [Q^{(n-m)}]_{kl} = R \sum_{k}^{s} Q_{ik} T_k \qquad (29)$$

where $$T_k = \sum_{l=1}^{s} [Q^{(n-m)}]_{kl} \qquad (30)$$

The conditional probability distribution of the second part of the path, given the first part (Eq. 25) is then, from Eq. 22 and Eq. 29, $$p(\gamma_{cb}|\gamma_{ac}, I) = \frac{Q_{ij} Q_{x_m,x_{m+1}} \ldots Q_{x_{n-1},x_n}}{\sum_{k=1}^{s} Q_{ik} T_k}, \qquad (31)$$

since the common factor R cancels. This distribution represents a Markov chain because the probability for the second path $\{x_m \ldots x_n\}$ depends only on the previous location $x_{m-1}$ and not on any of the details of the path the particle took to get to that point. From Eq. 31 we can determine the probability that the path switches from the first path at $i = x_{m-1}$ to the second path at $j = x_m$. This is called the "transition probability" and is found from the basic rules of probability by summing Eq. 31 over the locations that are not of interest:

$$p_{ij} \equiv p(x_m|x_{m-1}, I) = \sum_{x_{m+1}} \ldots \sum_{x_n} p(\gamma_{cb}|\gamma_{ac}, I) \qquad (32)$$

$$= \frac{Q_{ij}}{\sum_{k=1}^{s} Q_{ik} T_k} \left( \sum_{x_{m+1}} \ldots \sum_{x_n} Q_{j,x_{m+1}} \ldots Q_{x_{n-1},x_n} \right) \qquad (33)$$

where the term in parentheses is just $T_j$ of Eq. 30. Thus, the transition probability is $$p_{ij}^{(n,m)} = \frac{Q_{ij} T_j}{\sum_{k=1}^{s} Q_{ik} T_k} \qquad (34)$$

where the superscript notation is to remind us of the dependency on both n and m. This result was previously derived in the context of communication theory. This represents the maximum entropy transition probability between location $i=x_{m-1}$ and location $j=x_m$ for a path of length n.

Having derived the general case Eq. 34, the limiting case for $n \to \infty$ can be determined. The term both containing m and n is $T_k$ (Eq. 30), so we look at that first. The matrix Q can be reduced to block diagonal $\bar{Q}$ form as there exists a non-singular matrix B for which $\bar{Q} = B^{-1} Q E$ so that the powers of the matrix Q can be expressed as $$Q^n = B \bar{Q}^n B^{-1} \qquad (35)$$

so as $n \to \infty$ the element(s) $q_1^n$ of $Q^n$ dominate all others. In general, the roots $\{q_1, q_2, \ldots, q_r\}$ (assumed to be arranged in the order $|q_1| \geq |q_2| \geq \ldots \geq |q_r|$) of the characteristic equation $D(q) = \det(Q_{ij} - q\hat{o}_{ij})$ can be degenerate and complex. However, if $q_1$ is non-degenerate and real, then from Eq. 30 and Eq. 35

$$\lim_{n \to \infty} T_j = q_1^{(n-m)} \psi_{1j} \sum_{k=1}^{s} (B^{-1})_{1k} \qquad (36)$$

$\psi_1 \equiv B_1$ is an eigenvector of Q (the one with the largest eigenvalue) and $\psi_{1i}$ is the $i^{th}$ component of $\psi_1$. The denominator of Eq. 34 then contains a term $$\sum_{k=1}^{s} Q_{ik} T_k = \sum_{k=1}^{s} Q_{ik} \psi_{1i} = q_1 \psi_{1i} \qquad (37)$$

Using this and canceling common factors, the transition probability Eq. 34 in the limit of large n becomes:

$$p_{ij}^{(\infty)} = \frac{Q_{ij}}{q_1} \frac{\psi_{1j}}{\psi_{1i}} \qquad (38)$$

where $q_1$ is the maximum eigenvalue of Q and $\psi_{1i}$ is the $i^{th}$ element of the eigenvector $\psi_1$ associated with the maximum eigenvalue.

It is useful at this point to recall the parameter dependencies in Eq. 38. As noted above, the coupling matrix depends on the spatial locations Q(x) through the Lagrange multipliers. Thus, so do the eigenvectors: $\psi = \psi(x)$ and the associated eigenvalues q(x). In the examples shown below, the spatial dependence of these quantities is what produces the distribution maps directly from the eigenstructure of the lattice.

Eq. 38 appears similar to the expression for the transition matrix a priori introduced in (Eq. 5) but with several important differences. First of all, rather than being postulated it was obtained as a limit $n \to \infty$ from a more general expression Eq. 34. The derivation of Eq. 34 itself is general and depends on the sequence length n and the transition point $x_m$, both of which may be of arbitrary length (provided m<n). Further, it is not required that Q represent an adjacency matrix. If the Lagrange multipliers take the form $$\lambda_{ij} = \begin{cases} 0 & \text{connected} \\ \infty & \text{not connected} \end{cases} \Rightarrow Q_{ij} = e^{-\lambda_{ij}} = \begin{cases} 1 \\ 0 \end{cases} \qquad (39)$$

then Q becomes an adjacency matrix and Eq. 38 is identical to the expression (Eq. 5). Taking the Lagrange multipliers as "potentials", Eq. 39 can be viewed as representing local potentials that are either completely attractive ($\lambda = 0$) or completely repulsive ($\lambda = \infty$).

The entropy of the maximum entropy distribution Eq. 8, in the limit $n \to \infty$ can be obtained using the expression for the partition function $$Z = \sum_{i,j=1}^{s} [Q^n]_{ij} = Tr(Q^n) = \sum_{k=1}^{s} q_k^n \qquad (40)$$

{where $q_k$} are the roots of $|Q_{ij} - q\delta_{ij}|$. Taking $\lim_{n \to \infty} Z = q_1^n$ and using Eq. 15, the entropy per step becomes, from Eq. 8, $$\frac{S}{n} = \ln q_1 + \sum_{ij} \lambda_{ij} f_{ij} \qquad (41)$$

From Eq. 39, for the connected components $\lambda_{ij} = 0$, in which case Eq. 41 becomes $S/n = \ln q_1$, which is the same as the limit given by Burda, et. al. (*Phys. Rev. Lett.* 103, 160602 (2009)).

Localization:

In the special case that Q reduces to the adjacency matrix A (Eq. 39), an interesting property of the transition probability $p_{ij}^{(\infty)}(\gamma)$ in the limit $n \to \infty$ (the equilibrium transition probability) noted by Burda is that it localizes in what appears to be the largest accessible region of a defective lattice. They explained this effect by reformulating the problem in terms of a Hamiltonian equation, then making the analogy with Lifshitz spheres, defined as the largest spherical region of the lattice that is free of defects. We show here that this view is not correct in general.

It has been noted that the spatial distribution of the equilibrium probability density is described by the eigenvector $\psi^{(1)}$ associated with the maximum eigenvalue $q_1$ and thus localization can be investigated by looking at the structure of $\psi^{(1)}$. While it is possible to work directly in the eigen coordinates of the adjacency matrix $A\psi^{(k)} = q_k \psi^{(k)}$, it is useful and common to recast this in the form of a differential equation by noting that the adjacency matrix is related to the graph Laplacian by $L = D - A$. The elements of the diagonal degree matrix are $D_{ii} = d_i$, where $d_i$ is the vertex degree, and thus $$L\psi^{(k)} - D\psi^{(k)} = -q_k \psi^{(k)} \qquad (42)$$

In an undirected graph where edges have no orientation (which is all we will consider here), the degree is the number of edges incident to the vertex. For graphs that in the absence of defects are regular, every vertex has the same degree $d_{max}$. Then, vertices with defects have d=0 and those with d<$d_{max}$ are adjacent to defects. Adding $d_{max} \psi^{(k)}$ to each side of Eq. 42 and noting that the graph Laplacian is the negative of the Laplacian operator $\Delta$ for the Dirichlet boundary conditions considered here, yields the differential equation $$-\Delta\psi + V\psi = E_k\psi \tag{43}$$

where $V_j = d_{max} - d_j$ is the "potential" and $E_k = d_{max} - q_k$ is the "energy". The potential V is a vector of length n=length($\psi$) and V$\psi$ in Eq. 43 is an n-dimensional vector whose $j^{th}$ element is $V_j\psi_j$. Spatial variations in the potential are thus encoded through the components $V_j$. Eq. 43 has the familiar form of a Hamiltonian equation $\mathcal{H}\psi = E_k\psi$ where $\mathcal{H} = \Delta + V$. The addition of $d_{max}\psi$ to both sides of Eq. 42 allows the interpretation of $\psi^{(1)}$ of Eq. 43 as the ground state wavefunction, since $E_1 = d_{max} - q_1$ is the lowest energy because $q_1$ is the largest eigenvalue.

While the spatial distribution of the equilibrium MERW probability is encoded in $\psi_1$ the higher order MERW eigenfunction convey important information, as we shall demonstrate. Thus, while it is possible to examine Eq. 43 in the context of Lifshitz potentials, it is perhaps more illuminating to recognize that this equation expresses the fact that the eigenvectors of the adjacency matrix are the different energy modes of the Laplacian with boundary conditions determined by the potentials. This viewpoint permits a clear understanding of the localization phenomenon, and will further inform our understanding of the dynamics.

Figure 4A:
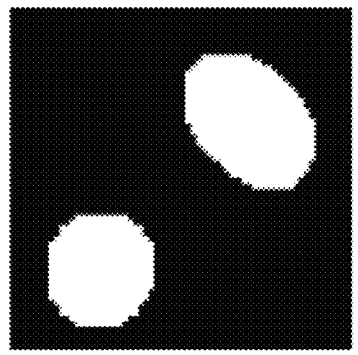
FIGS. 4A-4E show an exemplary adjacency matrix $Q_{ij}$ and eigenvectors $e_1$ to $e_4$ (arranged in decreasing order) for a periodic square lattice containing both a disk and an ellipse.
Figure 4B:
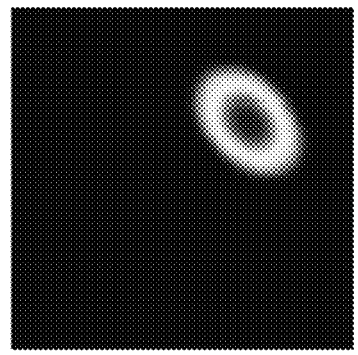
Figure 4C:
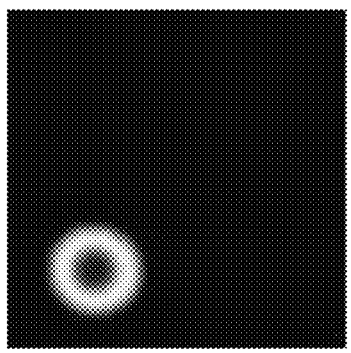
Figure 4D:
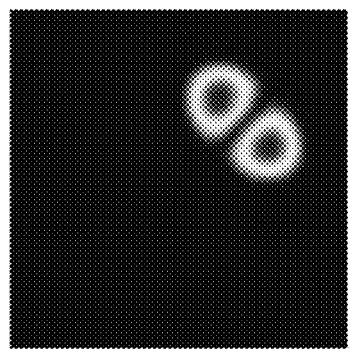
Figure 4E:
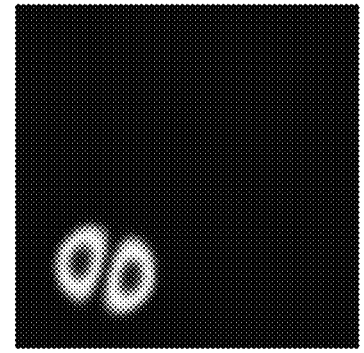

To illustrate this view, we consider localization examples of the disk and the ellipse, shown in FIG. 4A, where FIG. 4A shows the adjacency matrix $Q_{ij}$. The eigenvalues of the spherical region were chosen to be $\lambda = 10$ pixels, and those of the elliptical region to be $\{\lambda_1, \lambda_2\} = \{9, 14\}$, so that the largest spherical region is the disk, but the largest eigenvalue of the adjacency matrix belongs to the lowest mode of the elliptical region. FIGS. 4B-4E show eigenvectors $e_1$ to $e_4$, respectively, for a periodic square lattice of size L×L (L=64) containing both the disk and the ellipse, arranged in decreasing order of their eigenvalues $\lambda_i$. The eigenvectors distinguish separately the two regions and rank their relative modes according to their eigenvalues, and are the eigenvectors for the individual shapes. The first eigenvalue (FIG. 4B) determines the maximum entropy solution which is evidently not determined by the largest spherical region, but rather the largest eigenvalue of the Laplacian for these bounded regions (i.e., the ellipse). This contradicts the claim by Burda that the maximum entropy solution is the one in the largest spherical region.

Thus there are in fact multiple localization regions within the lattice, ranked according to the corresponding eigenvalues. It is therefore the spectrum of the maximum entropy eigenvectors, in descending order of the associated eigenvalues, which describes the information flow in the lattice. This flow occurs via a multitude of paths over multiple spatial scales of the lattice, hence the name "entropy spectrum pathways", or "ESP." In practical applications, the lattice can be described in terms of in pathways constructed from the first m eigenvectors of the adjacency matrix (in decreasing order of the eigenvalues which, from Eq. 38, is $$p_{ij}^{(\infty)} = \sum_{k=1}^{m} p_{ijk}^{(\infty)} \tag{44a}$$

where $$p_{ijk}^{(\infty)} = \frac{Q_{ij}}{q_k} \frac{\psi_j^{(k)}}{\psi_i^{(k)}}. \tag{44b}$$

For each transition matrix Eq. 44b there is a unique stationary distribution associated with each path k:

$$\mu^{(k)} = [\psi^{(k)}]^2 \tag{45}$$

that satisfies $$\mu_i^{(k)} = \sum_j \mu_j^{(k)} p_{ijk}^{(\infty)}, \tag{46}$$

the first of which $\mu_i^{(1)}$ corresponds to the to the maximum entropy stationary distribution.

Figure 5A:
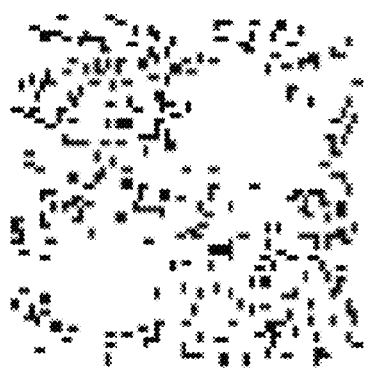
FIGS. 5A-5E show an exemplary adjacency matrix $Q_{ij}$ and eigenvectors $e_1$ to $e_4$ (arranged in decreasing order) for a periodic square lattice containing both a disk and an ellipse and random defects.
Figure 5B:
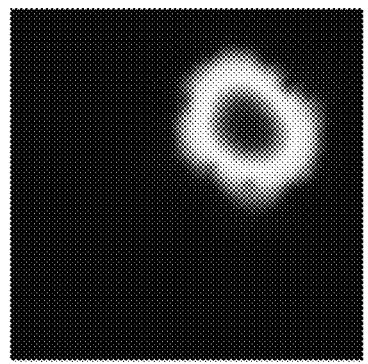
Figure 5C:
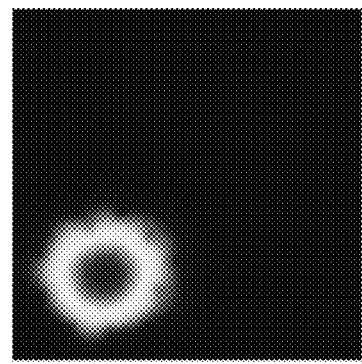
Figure 5D:
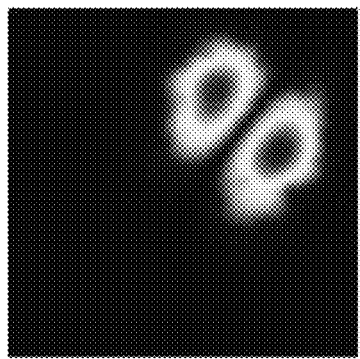
Figure 5E:
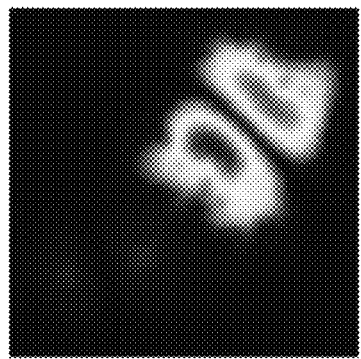

The localization phenomenon in a random lattice can now be made clear by combining a random lattice with the perfect disk and ellipse of FIG. 4A, as shown in FIG. 5A. The eigenvectors, shown in FIGS. 5B-5E, are then distorted versions of the idealized lattice in FIG. 4A caused by the alteration in the boundary conditions. The transition probabilities Eq. 38 and Eq. 44a determines the dynamics towards the equilibrium distribution $p_t^\infty$ through the update formula $$p_{t+1} = p_{ij} p_t \tag{47}$$

Figure 7A:
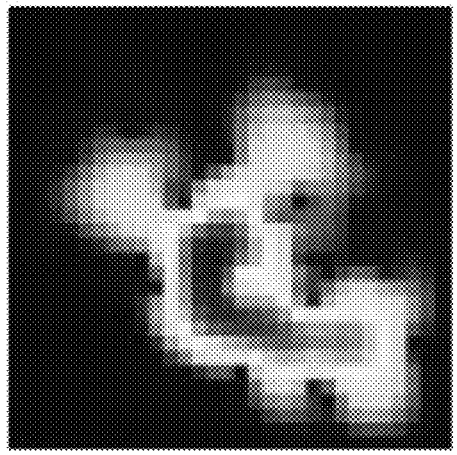
FIGS. 7A-7D show the four eigenvectors of the lattice in FIG. 6A using ESP.
Figure 7B:
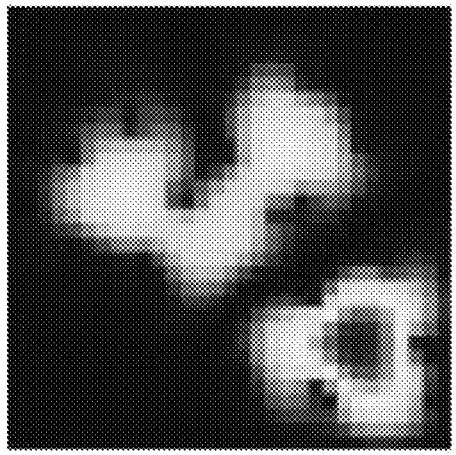
Figure 7C:
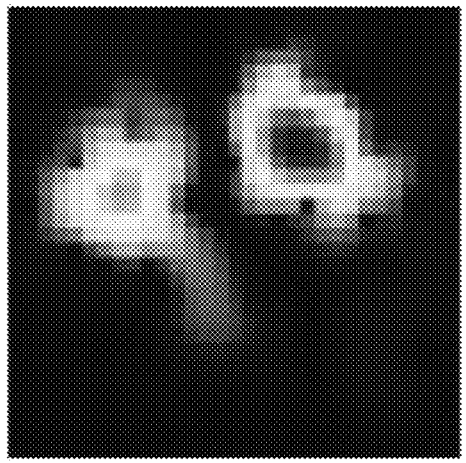
Figure 7D:
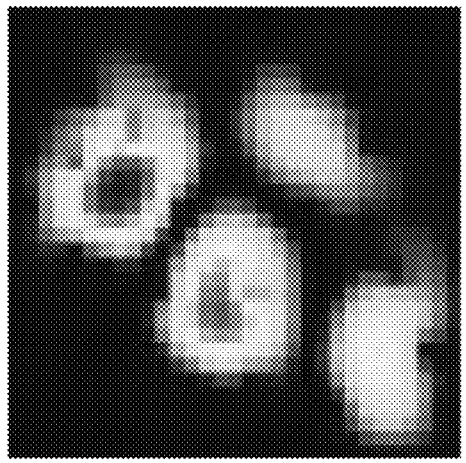

In the lattice FIG. 6A (with associated lattice degrees FIG. 6B), a point distribution (FIG. 6C) for the GRW (FIGS. 6E-6F) evolves into a relatively uniform spatial distribution, disrupted only locally by the defects. The MERW (FIGS. 6G-6H), on the other hand, "flows" to the equilibrium distribution. We emphasize that both FIGS. 6E-6F and FIGS. 6C-6H are generated by maximum entropy distributions, but with different prior information. The marked difference in these dynamics is purely a consequence of different prior information and, as such, can be viewed as a model of information flow, rather than the realization of a physical process. Further, while the dynamics in FIGS. 6E-6H were generated only from the primary eigenvector (FIG. 7A), in lieu of Eq. 44b, there exist multiple levels of information and associated pathways, as demonstrated in FIGS. 7B-7D.

While Eq. 47 provides a method to compute the information flow in the lattice, it provides little insight into how the macroscopic structure of the pathways is related to the microscopic dynamics of the information flow. One possibility to introduce this relation (due to Jaynes (*Complex Systems—Operational Approaches in Neurobiology, Physics, and Computers*, edited by H. Haken (Springer-Verlag, Berlin, 1985) pp. 254-269), albeit in a highly abbreviated form) is "bubble dynamics", in which the spatial-temporal characteristics of a probability density P(x 1 . . . xm; t) of a set of macroscopic variables X i, i=1, . . . , m, is characterized by the conservation of probability $$\partial_t P + \nabla J_I = 0 \tag{48}$$

where the information flux $J_I$ is the sum of a diffusive component $J_d = -D\nabla P$ and a convective component $J_c = -LP\nabla S$:

$$J_I = J_d + J_c \tag{49}$$

and S(x)=k ln W(x) is the entropy in which W(x) is the density of states, D is the diffusion coefficient (or, more generally, the diffusion tensor), and L=$\kappa$D (where $\kappa \equiv k^{-1}$ is the Onsager coefficient). Here x refers to spatial coordinates, on k, which is Boltzmann's constant in thermodynamics, just scales the entropy to the macroscopic variable space. Onsager coefficients are thus diffusion coefficients scaled to the spatial coordinates. Substitution of Eq. 49 into Eq. 48 gives $$\partial_t P + L\nabla \cdot (P\nabla S) = D\nabla^2 P \tag{50}$$

This is the Fokker-Planck equation with the potential equal to the entropy: V=S, and connects the global structure of the probability with the local structure of the lattice through the local structure of the entropy. Eq. 50 was previously derived (in a slightly different form) by Grabert and Green, (*Physical Review A* 19, 1747 (1979). It can be shown that Eq. 50 accurately describes the dynamics of the ESP, such as that illustrated in FIGS. 6E-6H, reproducing not only the accurate final ESP distribution but the flow of information through the lattice from an initial point distribution of FIG. 6C. This formulation can show that information flow occurs not only over different spatial scales, but over different temporal scales as well.

In order to investigate the dynamics via Eq. 50 we need to construct the entropy S. Having determined the maximum entropy transition matrix $P_{ij}^\infty$ (Eq. 38) between an initial point i and a final point j on the lattice, we want to construct the entropy map by calculating the entropy for every path $x_{ij}$ between these two points. This amounts to calculating the matrix $$S_{ij} = -\sum_{\{x_{ij}\}} p(x_{ij}) \ln p(x_{ij}) \qquad (51)$$

We then utilize a theorem by Ekroot and Cover (*IEEE Trans. on Inform. Theory* 39, 1418 (1993)) to construct the entropy map for all paths between a specified initial and final lattice locations. This theorem demonstrates that the matrix Eq. 51 can be computed directly from the transition matrix $p_{ij}$ and the equilibrium distribution μ from the expression $$S = K - \tilde{K} + S_\Delta \qquad (52)$$

where $K=(I-P+B)^{-1}(S^*-S_\Delta)$ in which I is the identity matrix, P is the transition matrix, and $\tilde{K}_{ij}=K_{jj}$, $B_{ij}=\mu_j$, $S^*_{ij}=S(p_{ij})$ and $$(S_\Delta)_{ij} = \begin{cases} h/\mu_i & i=j \\ 0 & i \neq j \end{cases} \qquad (53)$$

where h is the entropy per step in the limit n→∞:

$$h = -\sum_{i,j} \mu_i p_{ij} \ln p_{ij} \qquad (54)$$

and $S(p_i)$ is the entropy of the first step of a trajectory initially at location i, given by $$S(p_{ij}) = -\sum_j p_{ij} \ln p_{ij} \qquad (55)$$

The columns of S correspond to spatial maps of maximal entropy pathways from each point in the image to the target points and thus reveal preferred pathways throughout the image volume. This procedure can be done for any other of the k modes using $p_{ijk}^\infty$ (Eq. 44b).

Figure 8A:
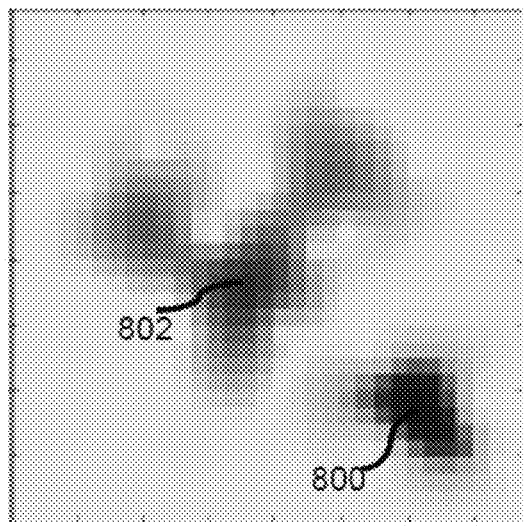
FIGS. 8A-8C illustrate the path entropy S(x, y) (FIG. 8A) from the initial distribution location of FIG. 6C to every other location and its spatial first and second derivatives (FIGS. 8B and 8C, respectively).
Figure 8B:
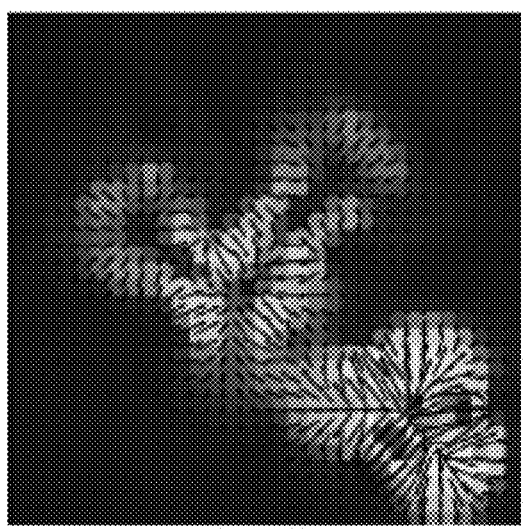
Figure 8C:
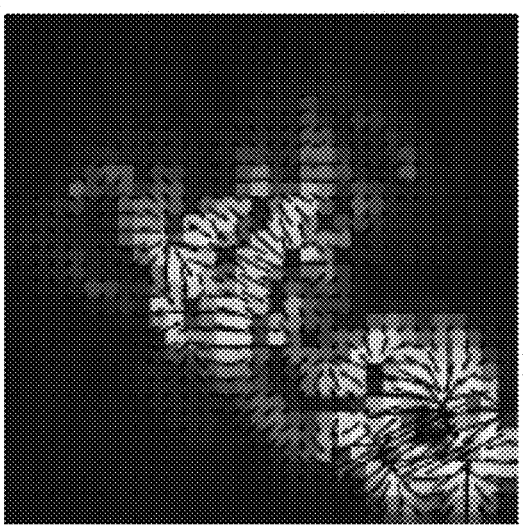

Using this construction, the path entropy S(x,y) (Eq. 51) from the initial distribution location FIG. 6C to every other location can be determined (FIG. 8A) and from this can be determined the first and second spatial derivatives (FIG. 8B and FIG. 8C). Note that the map has the characteristics of a source (at the low entropy (blue) starting region 800 and a sink at the high entropy (red) destination region 802.

Figure 9A:
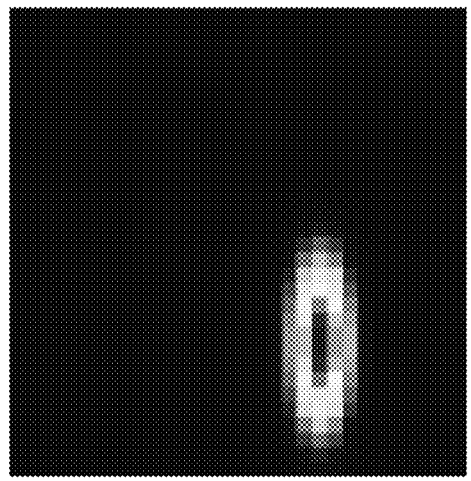
FIGS. 9A-9C show the time-varying distribution P(x, y, t) for the path entropy of FIG. 8A at three successive time points, $t_1$, $t_2$, $t_3$.
Figure 9B:
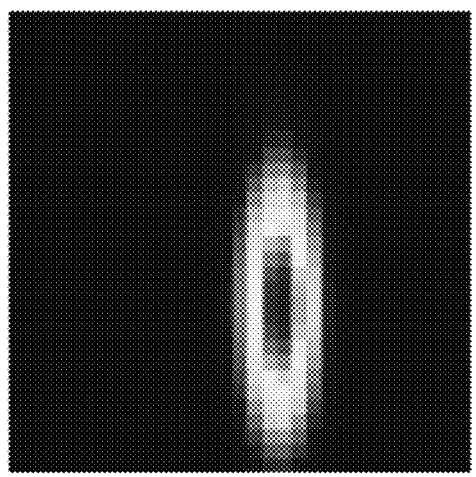
Figure 9C:
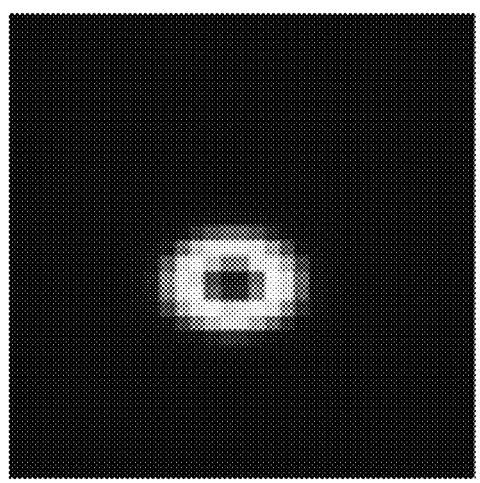

The time-varying distribution P(x,y,t) for the path entropy FIG. 8A is shown in FIGS. 9A-9C. The starting distribution follows the maximum entropy path shown in FIGS. 6G and 6H. The initially localized distribution moves and spreads in accordance with the local entropy field structure, then stalls and tightens at the maximum entropy location (the dark red region 802 in FIG. 8A), and the location of the highest probability concentration of $P_t^\infty$ (FIG. 6D).

The presented formalism can be used for finding static relations and for assessing dynamical information flow in many real world situations. With the ever-increasing number of applications in which connectivity plays a critical role (social networks, brain function and structure, etc.), methods for quantitative assessment of connectivity measures will play an increasingly significant role in a wide range of applications.

As an illustration of possible applications, we have included one practical example of ESP processing of magnetic resonance diffusion tensor imaging (MR-DTI) data. DTI data is often used for neural fiber tractography in the studies of brain connectivity. This is a complex and severely ill-posed problem. Within an imaging volume, local (voxel) DTI data measurements are used to reconstruct a (possibly high dimensional) tensor in each voxel that is able to capture some broad aspects of the underlying tissue microstructure, but on a scale much greater than the fibers themselves. From these tensor estimates are reconstructed the proported pathways of neural fiber bundles throughout the brain that produced the underlying variations in the diffusion signal. Imaging resolution is never (currently) fine enough to resolve individual fibers and thus individual voxel measurements are degraded by averaging over fiber bundles, possibly at different orientations, and other tissue compartments. Given the great complexity of the neural structure of the human brain, reconstruction of the macroscopic neural pathways from large volumes of noisy, highly multidimensional tensors derived from measurements of microscopic signal variations poses a significant theoretical and computational challenge.

The reconstruction of the macroscopic neural fiber pathways from the microscopic measurements of the local diffusion from DTI data is precisely the type of problem suited for the ESP formalism. The goal is to determine the most probable global pathways (neural fibers) consistent with measured values (diffusion tensors) based upon the available prior information. The ESP formalism provides a general method for the incorporation of prior information regarding the relationship between voxels. While the current description is limited to the nearest neighborhood coupling discussed in detail above, those of skill in the art will recognize that this is but one possible realization of the method. For the nearest neighbor coupling, the local potential can be derived from the interaction of the tensors, which is chosen here to be their inner product.

Figure 10A:
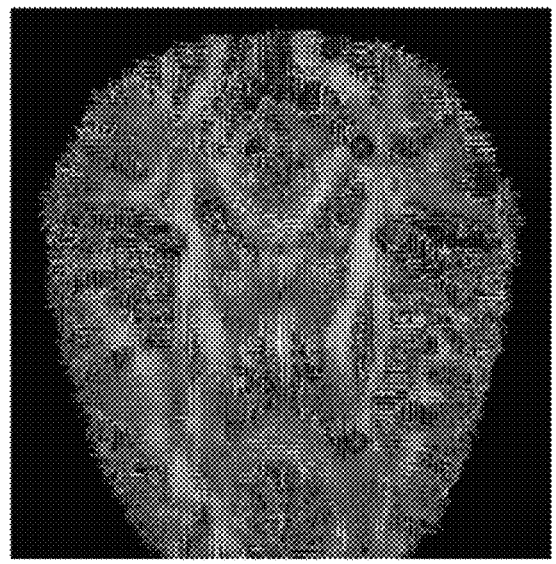
FIGS. 10A-10C illustrate the application of ESP to neural fiber tractography using diffusion tensor magnetic resonance imaging (DT-MRI) and comparison with the generic uniform random walk (GRW).
Figure 10B:
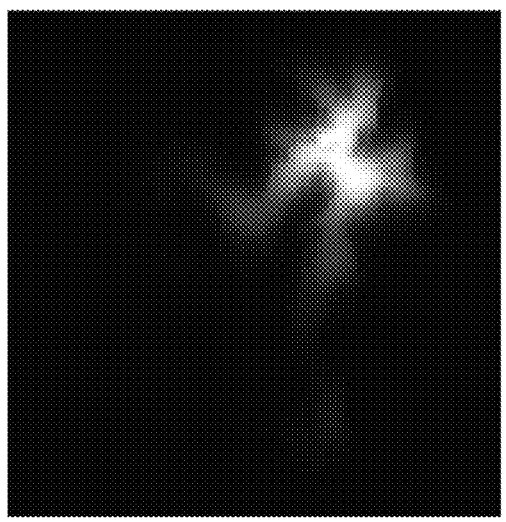
Figure 10C:
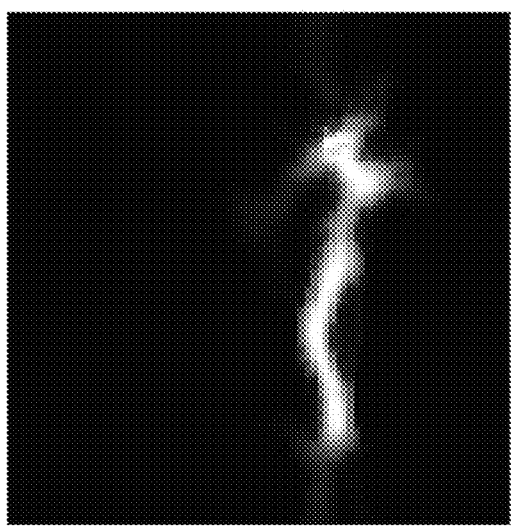

FIGS. 10A-10C provide an example of the application of ESP to neural fiber tractography using diffusion tensor magnetic resonance imaging (DT-MRI) and comparison with the generic uniform random walk (GRW). Data were collected on a normal human subject on a 3T GE Excite MR system with an 8-channel phase-array head coil using a spin echo echo-planar acquisition optimized for minimum echo time and the reduction of eddy current artifacts. Diffusion weighted images were collected along 61 gradient directions distributed according to the electrostatic repulsion model at a b-value of b=1500 s/mm². The acquisition parameters were: TE/TR=93/10, 900 ms, FOV=240 mm, NEX=1, matrix=128×128 with 34 contiguous 3 mm slices. Two field maps were collected for unwarping to correct for signal loss and geometric distortion due to B0 field inhomogeneities. Total scan time including field maps was approximately 16 minutes. The figure provides a quick comparison of the final trajectory generated between two chosen points by ESP (FIG. 10C) and GRW (FIG. 10B) (using the same number of time steps nt=500). A composite map of FA overlayed with the principal eigenvectors is shown for a single slice in FIG. 10A.

The presented example clearly shows a "global" nature of the ESP method, in the sense that it probes the most probable of all possible paths between the two points and the optimization is based on the entropy of the entire path, which depends upon all of the possible connections in all of the possible paths. One important advantage as demonstrated here is that the neighborhood of the path is explicitly taken into account. Different coupling schemes can produce different trajectory calibers. The method is quite general and can incorporate more sophisticated models of both inter-voxel diffusion anisotropy, such as high angular resolution reconstruction, and intravoxel coupling schemes, such as long range correlations.

Example 1

Tractography Guided by ESP

A critical simplification that is made in all current methods used to estimate either the intravoxel diffusion characteristics (via the EAP, for example) or to estimate the underlying global structure (tractography) is the assumption that these two estimation procedures are independent. Thus, one first estimates the intravoxel diffusion, then applies a tractography algorithms. For example multiple b-shell effects, used in obtaining the EAP, are used only to infer directional multiple fiber information for input into streamline tractography algorithms. However, this distinction between local and global estimation is artificial and limiting, since both the local (voxel EAP) information and the global structure (tracts) are from the same tissue, just seen at different scales.

The problem of local diffusion estimation and fiber tractography is revisited with the specific goal to include multiple spatial and temporal scales that can be deduced from multiple b-shell DW-MRI measurements in addition to just angular (multi-)fiber orientation. In many practical applications, either one or two spatial locations (or regions) are known a priori. In neuroscience applications, for example, two regions may be functionally connected (as measured, perhaps, by FMRI) and the diffusion weighted MRI data is being used to assess the degree (if any) of the structural connectivity between two functionally connected regions. We therefore reconsider two common formulations of fiber tractography: (1)—initial value, i.e., finding fibers that start at some chosen area of the brain; and (2)—boundary value, i.e., finding fibers that connect two preselected brain regions. Thus, we recast the fiber tractography algorithm as the determination of the most probable path either starting at a selected location or connecting two spatial locations, and seek a general probabilistic framework that can accommodate various local diffusion models and yet can incorporate the structure of extended pathways into the inference process. In this case, the problem of tractography from DWI data can be reformulated as the determination of the probability of paths on a 3D lattice between two given points where the probability of a path passing through any particular point is not equiprobable, but is weighted according to the locally measured diffusion characteristics.

The essential problem at the core of the tractography problem is the estimation of macroscopic structure from microscopic measurements. In this example, we present a formulation of the tractography problem based upon entropy spectrum pathways (ESP). The ESP method is generalized to utilize multi-scale diffusion information that is available in multi-shell DWI datasets by extending the mechanism of streamlines generation using a Hamiltonian formalism and a diffusion-convection (Fokker-Plank) description of signal propagation though multiple scales.

The ESP framework allows for the incorporation of both measured data and prior information into the estimation procedure. It is therefore essential that the description of the data be as general and complete as possible. A general description of the measured DW-MRI data is provided by the EAP formalism. (See, e.g., M. Descoteaux, et al., "Multiple q-shell diffusion propagator imaging," Med. Image Anal., vol. 15, no. 4, pp. 603-621, August 2011.) In this example, we reformulate the problem in order to provide a general characterization amenable to numerical implementation, and to bring out some of the essential spatial scales that inform the application of ESP.

Figure 11:
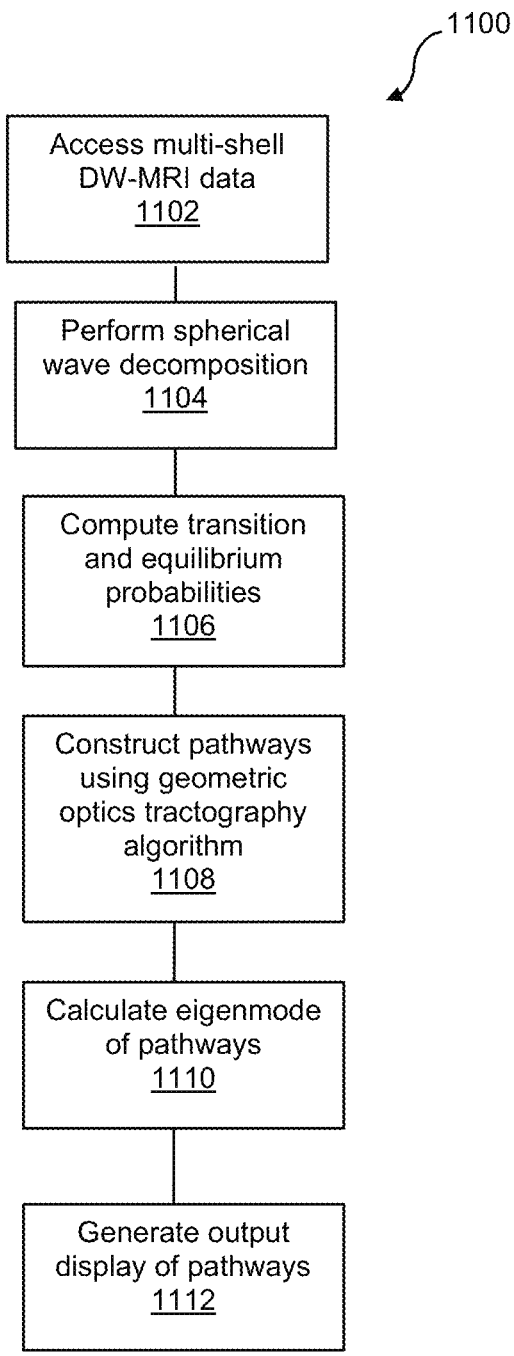
FIG. 11 is a block diagram illustrating basic steps of the inventive approach to fiber tractography.

The basic process for application of the inventive approach to fiber tractography are illustrated in the block diagram 1100 of FIG. 11. The process, components of which will be described in detail in the following discussion, includes, in step 1102, obtaining and inputting into a computer processor measured a diffusion-weighted MRI signal using a multiple b-value acquisition with uniform angular resolution at each b-value, i.e., multi-shell acquisition, as is known in the art. In step 1104, spherical wave decomposition is performed on the DW-MRI data. A coupling matrix is generated for diffusion connectivity at various scales using the spherical wave decomposition coefficients. In step 1106, the transition probability and equilibrium probability are computed. The transition probabilities are used to represent the angular and scale distributions of the pathways. Next, pathways are constructed using a geometric optics tractography algorithm in step 1108. The eigenmodes of the pathways are calculated in step 1110, and the results are output to a graphical display in step 1112. Sample outputs are provided in FIGS. 18A-21F.

In step 1102, the DW-MRI signal W(r, q) measured in both r and q space can be expressed in terms of both the spin density ρ(r) and the average propagator $p_A(r, R)$ using the narrow pulse approximation as $$W(r,q) = \int Q(r,R) e^{-iq \cdot R} dR \qquad (56)$$

where r is the voxel coordinate, $q = \gamma G \delta / 2\pi$, with G and δ being the strength and duration of the diffusion-encoding gradient and γ the gyromagnetic ratio of protons and the function W(r, q) is the Fourier transform (in the diffusion displacement coordinate R, defined as a change in particle position over time t, $R = r(t_0 + t) - r(t_0)$) of the weighted spin density function $$Q(r,R) = \rho(r) p_A(r,R) \qquad (57)$$

that scales (or weights) the spin density with the average propagator $p_A(r, R)$ at each observed voxel.

In step 1104, to find an expression for the spin density function Q(r, R) we will use the plane wave expansion in spherical coordinates with $q = q\hat{q}$ and $R = R\hat{R}$, where $q = \|Q\|$ and $R = \|R\|$, $$e^{i q \cdot R} = 4\pi \sum_{l=0}^{\infty} \sum_{m=-l}^{l} i^l j_l(qR) Y_l^{m*}(\hat{q}) Y_l^m(\hat{R}) \tag{58}$$

where $j_l(qR)$ is the spherical Bessel function of order l and $Y_l^m(\hat{q})=Y_l^m(\Omega_{\hat{q}})=Y_l^m(\theta_q, \phi_q)$ is the spherical harmonic with $\theta_q$ and $\phi_q$ being the polar and azimuthal angles of the vector q, and similarly for the vector R.

The product $j_l(qx)Y_l^m(\hat{x})$ represents the basis function for the spherical wave expansion. These basis functions can be obtained as solutions of Helmholtz's wave equation:

$$\nabla^2 f + q^2 f = 0, \tag{59}$$

This representation suggests an interesting possibility of treating the problem of fiber tractography for diffusion weighted MRI data using the techniques of geometrical optics in inhomogeneous media.

The above basis functions are composed of radial (spherical Bessel $j_l$) and angular (spherical harmonic $Y_l^m$) parts, where the spherical harmonics $Y_l^m(\hat{x})$ are the eigensolution of the angular part of the Laplacian with the eigenvalues $\lambda_l = -l(l+1)$:

$$\nabla_\Omega^2 Y_l^m = \lambda_l Y_l^m. \tag{60}$$

The spherical harmonic $Y_l^m$ of degree l and order m allows separation of the $\theta$ and $\phi$ variables when expressed using associated Legendre polynomials $P_l^m$ of order m as $$Y_l^m(\theta, \phi) = c_{l,m} P_l^m(\cos\theta) e^{-im\phi} \tag{61}$$

where $c_{l,m}$ is the normalization constant $$c_{l,m} = \sqrt{\frac{2l-1}{4\pi} \frac{(l-m)!}{(l+m)!}}.$$

chosen to guarantee the orthonormality condition $$\int_0^\pi \int_0^{2\pi} Y_l^m Y_{l'}^{m'*} \sin\theta \, d\theta \, d\phi = \delta_{ll'} \delta_{mm'}.$$

The radial component $j_l(qx)$ of Eq. 58 is obtained as the eigenfunction of the radial Laplacian $$\nabla_r^2 j_l = -\left(q^2 + \frac{\lambda_l}{r^2}\right) j_l, \tag{62}$$

with the orthonormality conditions $$\int_0^\infty j_l(qx) j_l(q'x) x^2 \, dx = \frac{\pi}{2q^2} \delta(q-q').$$

This allows us to reconstruct the spin density function $Q(r, R)$ using the spherical wave decomposition as $$Q(r, R) = 4\pi \sum_{l=0}^{\infty} \sum_{m=-l}^{l} i^l Y_l^m(\hat{R}) s_{lm}(r, R), \tag{63}$$

where $$s_{lm}(r, R) = \int W(r, q) j_l(qR) Y_l^{m*}(\hat{q}) \, dq. \tag{64}$$

This representation offers a concise and intuitively clear quantitative description of the local diffusion in terms of a clearly defined expansion order on which can be based decisions of optimal fitting. It may be noted that finding the best representation of q-signal on partially acquired grid was not an intent of the above exercise, and that existing fast and robust algorithms previously disclosed by the inventors in International Publication No. WO2015/039054 A1 (incorporated herein by reference) were used for this computation. This implementation is flexible and provides a choice of several filters that can significantly reduce ringing artifacts.

It should be kept in mind that the typical scales for the voxel coordinate r and for the dynamic displacement R in current diffusion weighted MR experiments are vastly different. For the time scale over which the individual measurements in DWI are typically made ($\approx$50 ms), the free diffusion root mean squared distance is $\langle x^2 \rangle^{1/2} \approx 20\mu$ and thus much smaller than typical voxel dimensions ($\approx$1 mm$^3$, at best). Hence, with high degree of accuracy it can be assumed that the average propagator in the spin density function Q(r, R) only influences the nearest neighbor voxels through the dynamic displacement R dependence. The entropy spectrum pathway (ESP) formalism presented herein is well suited for taking nearest neighbors into account.

As previously described, the ESP method is an extension of the maximum entropy random walk and concerns the very general problem of random walks on a defective or disordered lattice. ESP provides several key findings: first, the pathways of the random walk are determined by prior information concerning the structure and relationships of the lattice points, and therefore the ESP represents a flow of information, rather than representing an actual physical process. This view facilitates the use of ESP within a wide range of practical problems related to connectivity. Second, it is possible to characterize multiple pathways, ranked according to their entropy, all of which contribute to the flow of information on the lattice. Thirdly, the interesting localization phenomenon previously noted can be understood in terms of the eigenstructure of the lattice. Fourthly, the local interactions that inform the generation of global structure can be based upon whatever coupling information the user has available. This coupling can take on a general form, and it was shown that this property can be understood in terms of potential theory. In the case of nearest neighbor coupling with a "binary" potential (on or off), the problem reduces to the computation of the eigenstructure of the adjacency matrix of accessible (non-defective) lattice locations. But the more general formulation of ESP facilitates the use in practical applications.

In the context of the tractography problem, the objective is to calculate the probability that a spin, or "particle", starting from an initial spatial location $x(t_0)$ at initial time $t_0=0$ diffuses to a second location $x(t)$ at a later time t. While the underlying structure we wish to estimate is assumed continuous (being comprised of tissue fibers), the spatial locations x at which the measurements are acquired are assumed to be from DWI images and thus discretized to a 3D Cartesian spatial grid. However, the temporal discretization to be employed is a fictitious construct used to implement a random walk model, due to the above mentioned difference in scales of the voxel coordinates and the dynamic displacement. Our space-time points are defined on the true voxel spatial grid but on a diffusion pseudo-time grid whose increments are much larger than the experimental time scale. Simulating diffusion in this way lends itself to two different interpretations. One view of this process is to see it as diffusion that is allowed to take place for much longer than the measurement time, or, equivalently, that the process is in equilibrium and thus long time behavior is well-represented by the snapshots in time provided by the experimental data. However, another viewpoint, that of ESP, and the one we adopt, is that the simulation is of the flow of information constrained by the physical measurements. The entire process is one of estimating macroscopic phenomena from local measurements, using prior information.

Application of the ESP theory to the present problem lies in its ability to rank multiple paths, and that these paths can be constructed from arbitrary coupling schemes through $Q_{ij}$. For each of the stationary distributions is associated a path related to the localization of information related to the eigenstructure of the disordered lattice (see Eq. 45). The key feature is that the local transition probabilities between nodes depend on the global structure of the graph through the eigenvectors $\psi^{(k)}$. In practical applications, the lattice can be described in terms of n pathways constructed from the first n eigenvectors of the potential matrix in decreasing order of the eigenvalues).

We do not presume to be explicitly modeling the diffusion over the paths, since we know that the diffusion length over the typical time-scale of a DWI experiment is typically far smaller than a voxel dimension. Rather, this procedure is viewed as one of estimation and thus the construction of the ranked maximum entropy paths—those that are most unbiased with respect to the measured data and the prior information (the lattice couplings) while satisfying the initial and/or final conditions. In this view, the problem is one of estimating the global connectivity from the local diffusion characteristics.

The estimation of the local and global tissue structure over multiple scales using DW-MRI data can be investigated within the ESP framework by viewing the data as measurements on a 3D lattice in which each voxel is ascribed a "potential" that is related to its coupling with neighboring voxels. An important feature of the ESP approach is that this potential is very general in form. This is critical to its application in the current problem. While it was shown for a binary coupling (i.e., wherein the coupling matrix reduced to the adjacency matrix with 0/1 elements), in the current problem we will incorporate a strength of coupling that reflects the local interaction of voxel data. In order to do this we first symmetrize the spin density function $$Q_{ij}(r_i,l)=Q_{ji}(r_j,l)=\tfrac{1}{2}[Q(r_i,(r_i-r_j)l)+Q(r_j,(r_j-r_i)l)], \quad (65)$$

where l represents the dimensionless ratio of scales of dynamic displacement R to the spatial (voxel) scales r, and, then sum all relevant scales included in the spin density function Q(r, R) by the dependence on the dynamic displacement R:

$$\overline{Q}_{ij}=\overline{Q}_{ji}=\int_{lmin}^{lmax} Q_{ij}(r_i,l)dl. \quad (66)$$

Here, we used a symmetric input from voxels i and j by taking the line integral of the spin density function $Q(r, R_l)$ along the direction $R_l=r_i-r_j$ between those voxels and take into account only a subset of spatial scales that can contribute to this interaction (from $l_{min}$ to $l_{max}$). Since the typical scales for the voxel coordinate r in current diffusion weighted MR experiments are much larger than the scales for the dynamic displacement R (20μ vs 1 mm), the coupling can be limited to nearest neighbor effects taking $l_{min}=0$ and $l_{max}=\infty$ to calculate a coupling potential $\overline{Q}_{ij}^{\infty}$. We would like to emphasize, that in nearest neighbor coupling evaluation (Eq. 66) we do not use solid angle integration. The appropriate choice of filters and order of angular resolution in the SWD allows us to replace the costly integration of geometrically complex coupling between noisy multiple peaked dODF from neighboring voxels with the fast and simple line integration across all radial scales. This form of the coupling potential is then used in Eq. 20 to obtain the relevant eigenvalues and eigenvectors $$\sum_j \overline{Q}_{ij}^{\infty} \psi_j^{(k)} = \lambda_k \psi_i^{(k)}. \quad (67)$$

In step 1106 of FIG. 11, the k-th eigenvalue and eigenvector can be used to generate the transition probabilities (Eq. 44b) but in addition, we also generate the scale dependent transition probabilities $$\mathcal{P}_{ijk}(r_i,l) = \frac{Q_{ij}(r_i,l)}{\lambda_k} \frac{\psi_j^{(k)}}{\psi_i^{(k)}}, \quad (68)$$

which will be equal to the total transition probability $P_{ij}$ when integrated over all scales l. As those probabilities only describe transitions between nearest neighbors they can be expressed as a scale dependent function $\mathcal{P}_i(r, R)$. We will also generate the equilibrium probabilities $\mu^{(k)}=[\psi^{(k)}]^2$.

To reiterate, the general problem of tractography is necessarily one of multiple scales because the local diffusion occurs on the microscale and the tracts are on a macroscale. The entire point of the ESP approach is that it enables a characterization of the problem in terms of information at these multiple scales.

The present goal is either to construct a pathway between an initial spatial location a and a final spatial location b or to trace a pathway incrementally starting from an initial location a. In both cases we are interested in "the most probable" pathways, i.e., we would like to constrain our local search by the global entropy structure. Therefore, our interest is not in the final equilibrium distribution μ* but in the pathway to it. We are therefore interested in the dynamics of the probability and want to compute the path that maximizes the entropy at each step, and thus results in the final (equilibrium) distribution μ* at time τ. The scale dependent transition and equilibrium probabilities obtained in the previous section can naturally define the global entropy field that shapes the flow of information and allow optimal paths to be found. In the limit of long pathway lengths (or large time τ) and under the Markovian assumption, the rate of entropy change $S_l(r_i)$ can be expressed at each location $r_i$ as $$S_l(r_i) = -\sum_k \mu^{(k)} \sum_j \mathcal{P}_{ijk}(r_i,l)\ln\mathcal{P}_{ijk}(r_i,l) \quad (69)$$

The most straightforward way to include this multiscale structure of the global entropy field is by taking into account that the conservation of probability in general includes not only the diffusive component (as for example used by Callaghan (*Principles of nuclear magnetic resonance microscopy*, Oxford Univer. Press, 1993) for obtaining the expression of EAP in single mode homogeneous self-diffusion), but also has the convective part $$\partial_t P + \nabla\cdot(LP\nabla S) = \nabla\cdot D\nabla P, \quad (70)$$

where P is the probability, S is the entropy, and L and D are coefficients (in general, either tensors or functions of the coordinates) that characterize local convective and diffusive scales (L=κD). This Fokker-Planck equation (also provided as Eq. 50), with the potential equal to the entropy, connects the global structure of the probability with the local structure of the lattice through the local structure of the entropy.

The current state-of-the-art approaches used for fiber tractography in DTI/DWI data require splitting this problem into two parts: first, obtain the EAP from the diffusion only subsystem, $$\partial_t P = \nabla_R \cdot D \nabla_R P, \quad (71)$$

and second, solve the convective part (averaged over all the dynamic displacement scales R)

$$\int [\partial_t P + \nabla_r \cdot (LP\nabla_r S)] dR = 0, \quad (72)$$

by simple local tracing of one (DTI) or several (DWI) principal fiber directions. Unfortunately, this decoupling results in only the local diffusion information derived from EAP being used at the fiber tracking stage.

To illustrate this point, we will first assume the entropy gradient fixed and will show how it leads to the current tractography. In this case, the convective part of Eq. 70 in the eikonal approximation provides a simple expression for the Hamiltonian $\mathcal{H}(w, k, r)$—the function of canonical coordinates that defines the dynamics. (For mechanical systems this function is simply the total energy, which is conserved in motion. For more complex systems it does not necessarily correspond to energy, but still describes conservation laws of the system).

$$\mathcal{H}(\omega, k, r) = \frac{1}{V_R} \int [-\omega^2 + (k \cdot L \nabla S)^2] dR, \quad (73)$$

where an input from all dynamic displacement scales is included, as formally both L and S may depend on both R and r. Finding the characteristics (or rays) of Eq. 70 will describe how the signals propagate and can be accomplished by integrating a set of ordinary differential equations of the Hamilton-Jacobi type:

$$\frac{dr}{dt} = \frac{\partial \mathcal{H}}{\partial k}, \quad \frac{dk}{dt} = \frac{\partial \mathcal{H}}{\partial r}. \quad (74)$$

The current fiber tractography methods in general do not emphasize or discuss the notion of global entropy, but implicitly assume the local behavior of the entropy gradient, directing it along some of the major axes of the local diffusion/convection tensor L=κD, i.e., $\nabla V = \psi$, where $\psi$ is the eigenvector of $L \cdot \psi = \lambda \psi$. Under the assumption of scale independent diffusion (i.e., D(r, R)≡D(r)) the Hamiltonian Eq. 73 then becomes $$\mathcal{H}(\omega, k, r) = -\omega^2 + \lambda^2 (k \cdot \psi)^2, \quad (75)$$

and the ray tracing equation simplifies to the following form $$\frac{dr}{dt} = \frac{\partial \mathcal{H}}{\partial k} = 2\lambda^2 (k \cdot \psi) \psi = C \psi. \quad (76)$$

Ignoring the spatial dependence of the diffusion propagator (i.e., C=const) this equation is exactly in the form of Frenet equation commonly used for fiber tracking. Thus, the current fiber tractography can be regarded as a fixed scale and spatially homogeneous limit of the more general Fokker-Planck formalism—Eqs. 50 and 70.

To develop a more general entropy-based tractography, several assumptions will be made. First, only solutions with the high enough probability will be considered, i.e., it will be assumed that in the region of interest the probabilities are sufficiently close to 1, so that it is possible to linearize both the probability and the entropy as $$P = P_0 + P_1, S = S_0 + S_1 = S_0 - (1 + \ln P_0) P_1, \quad (77)$$

where $S_0 = -P_0 \ln P_0$ and the scale dependent transition probability $\mathcal{P}_j(r, R)$ (Eq. 68) can be substituted for $P_0$. It is assumed that $P_1$ is a small correction to the equilibrium probability (i.e., $P_1 \ll P_0$). The linearized convective part of Eq. 70 can then be written $$\partial_t P_1 = \nabla \cdot (P_1 \nabla P_0 (2 + \ln P_0)) + \nabla \cdot (P_0 (1 + \ln P_0) \nabla P_1). \quad (78)$$

Use of the scale dependent transition probability $\mathcal{P}_j(r, R)$ for $P_0$ allows us to omit L in these expressions, as the diffusion anisotropy is already included in ESP calculations of $\mathcal{P}_j(r, R)$ from the spin density function Q(r, R) obtained with the spherical wave decomposition using Eqs. 63 and 64. No time dependence is assumed to be present in $P_0$ as it is time stationary, hence $\partial_t P_0 \equiv 0$. We have also omitted the last term $\nabla \cdot D \nabla P_1$ from the Eq. 70 as it will not appear in eikonal approximation used for obtaining the ray tracing equations.

Eq. 78 is a linear inhomogeneous hyperbolic equation, hence it has traveling wave solutions propagating along the characteristics. In order to formally find those characteristics we will assume a plane wave solution for $P_1$ in the form $$P_1(r, R, t) = A(r, R, t) e^{i \psi(r, t)}, \quad \psi(r, t) = k \cdot r - \omega t, \quad (79)$$

and then obtain a more general expression for the Hamiltonian as $$\mathcal{H}(\omega, k, r) = \frac{1}{V_R} \int [-\omega^2 + (k \cdot X)^2 + (Y(k \cdot k) - Z)^2] dR, \quad (80)$$

where $X = \nabla P_0 (2 + \ln P_0) + \nabla (P_0 (1 + \ln P_0))$, $Y = P_0 (1 + \ln P_0)$, $Z = \nabla \cdot \nabla P_0 (2 + \ln P_0)$, and again, again we averaged over all dynamic displacement scales.

Hence, in step 1108, taking into account the global entropy gradient as well as the scale dependence of the diffusion coefficient, the fiber tracking in the geometrical optics limit can be represented in more general form, using Eqs. 74 and 80, as $$\frac{dr}{dt} = \frac{2}{V_R} \int [X(k \cdot X) + 2kY(Y|k|^2 - Z)] dR, \quad (81)$$

$$\frac{dk}{dt} = -\frac{2}{V_R} \int [(k \cdot X) \nabla (k \cdot X) + (|k|^2 Y - Z)(|k|^2 \nabla Y - \nabla Z)] dR. \quad (82)$$

The first equation (Eq. 81) traces the characteristics (rays) of the convective part of the original Fokker-Plank equation (Eq. 70) under the influence of a local diffusion coupled with a global entropy gradient. This coupling is locally described by a vector X. A second term (with 2kY) provides some smoothing by adding "a push" in the direction of the wave vector k. It also ensures that in voxels with isotropic diffusion (or with many fibers of different directions crossing) and without a global entropy gradient, the ray will continue following this k direction. In the second equation (Eq. 82), the spatial gradients are responsible for a change of the wave vector k direction and magnitude.

The traditional approach defines tracts by integration of position-only function ψ, which assigns the tangential direction of tracts to each location r. For the geometrical optics approach, the integration takes into account both the orientation and multiple scales, through the dependence of ψ on directional angle k/|k| and magnitude |k|.

FIGS. 12A-12B provide a schematic illustration of traditional fiber tracking based on integration of a single Frenet equation (FIG. 12A) vs. fiber tracking that uses the geometrical optics analogy (FIG. 12B). In the first case, the fiber orientation vector ψ only depends on spatial location $r_0$, hence, even at the location of fiber crossing, only the single most important fiber can be followed (point $r_0$ uniquely selects a single family of fibers oriented along ψ($r_0$)). Referring to FIG. 12B, the geometrical optics approach automatically includes dependence of ψ on both orientation k/|k| and scale |k|, allowing it to effectively proceed through difficult areas of crossings of multiple fibers (the choice of fiber direction at point $r_0$ depends on the value of the parameter k, with $k_1$ selecting the same fiber direction as in FIG. 12A, and $k_2$ corresponding to the alternative crossing family of fibers).

Example 2

Tractography Guided by ESP—Evaluation

To evaluate practical aspects and performance of ESP-guided fiber tractography, we conducted several simulations of multiple shell multiple angle diffusion weighted MRI datasets acquired using either realistic MR phantom or real brain samples.

The first dataset is of the well-known "fiber cup" MR phantom extensively used for testing and performance evaluation of various fiber tractography approaches. The phantom consists of seven fiber bundles confined in a single plane by squeezing them in between two solid disks. Diffusion-weighted image data of the phantom was acquired on the 3T Tim Trio MRI system with 3 mm isotropic resolution on 64×64×3 spatial grid. Three diffusion sensitizations (at b-values b=650/1500/2000 s/mm$^2$) were collected two times for 64 different diffusion gradients uniformly distributed over a unit sphere. Several baseline (b=0) images were also recorded.

Our initial stage of processing includes restoration of the spin density function Q(r, R) using Eqs. 63 and 64. The spin density function is then used to generate symmetric scale integrated input to the coupling potential with Eqs. 65 and 66. Eigenvectors and eigenvalues of the coupling potential then used for obtaining the transition probabilities using Eq. 44b.

Figure 13A:
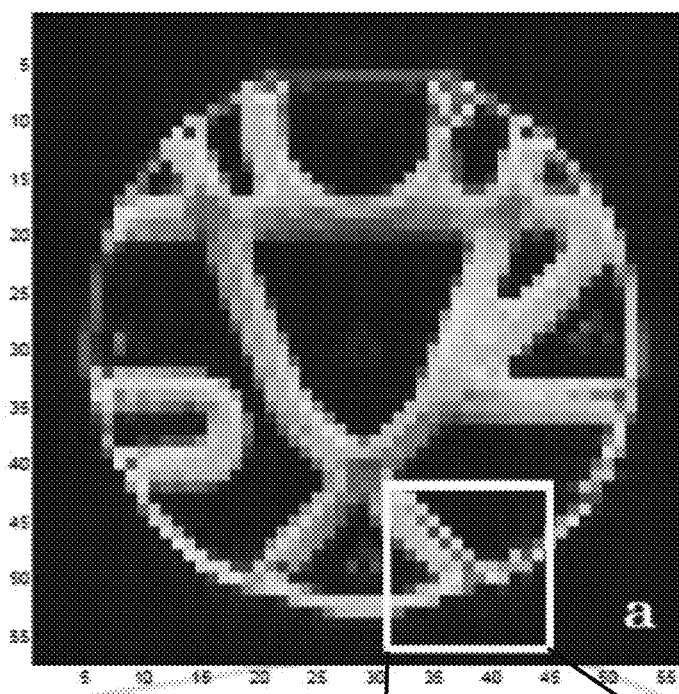
FIG. 13A is a baseline image of a phantom.
Figure 13D:
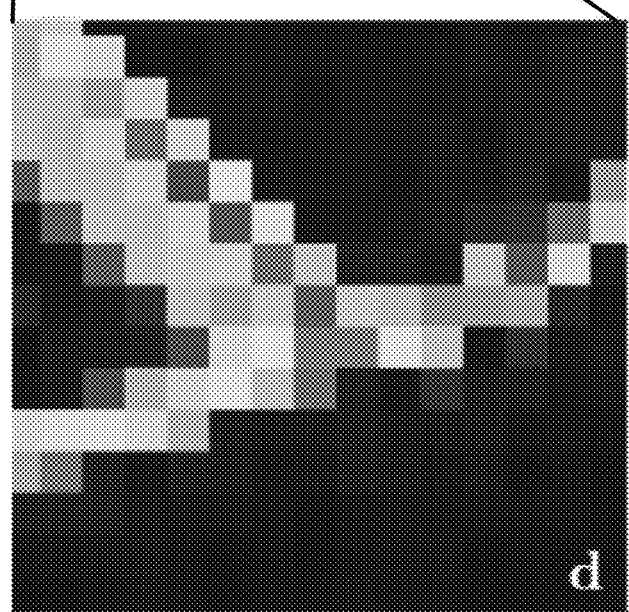
FIGS. 13D-13F are enlarged sections from FIGS. 13A-13C.
Figure 13B:
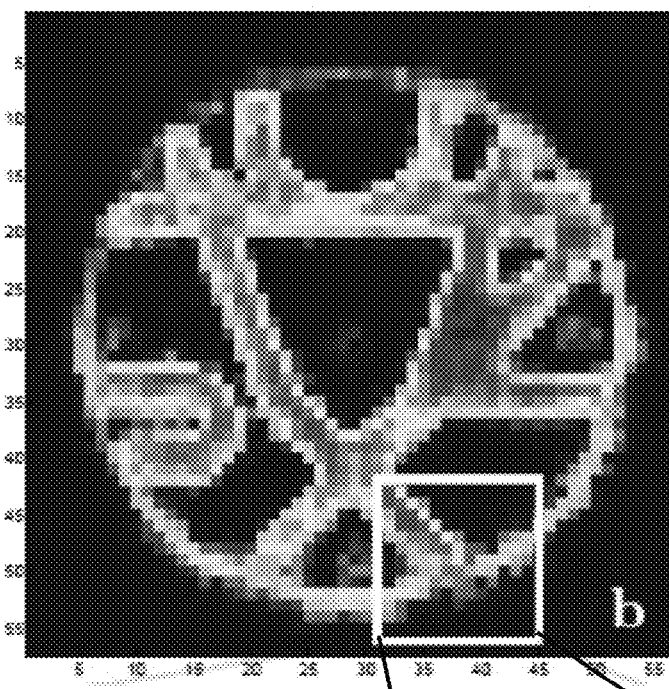
FIG. 13B is a map of the largest ESP transition probability values for the baseline image.
Figure 13E:
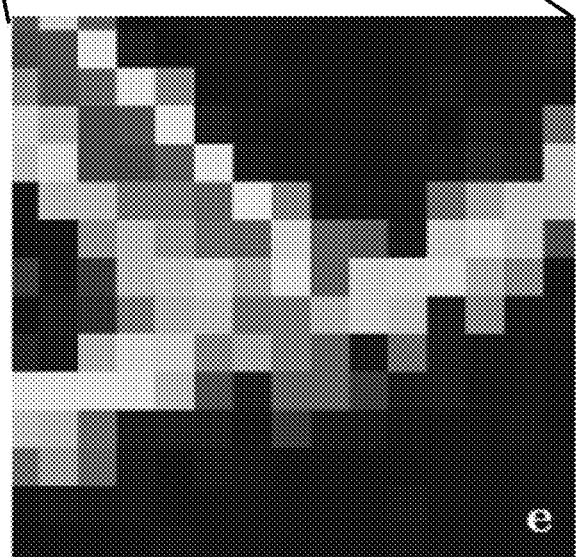
Figure 13C:
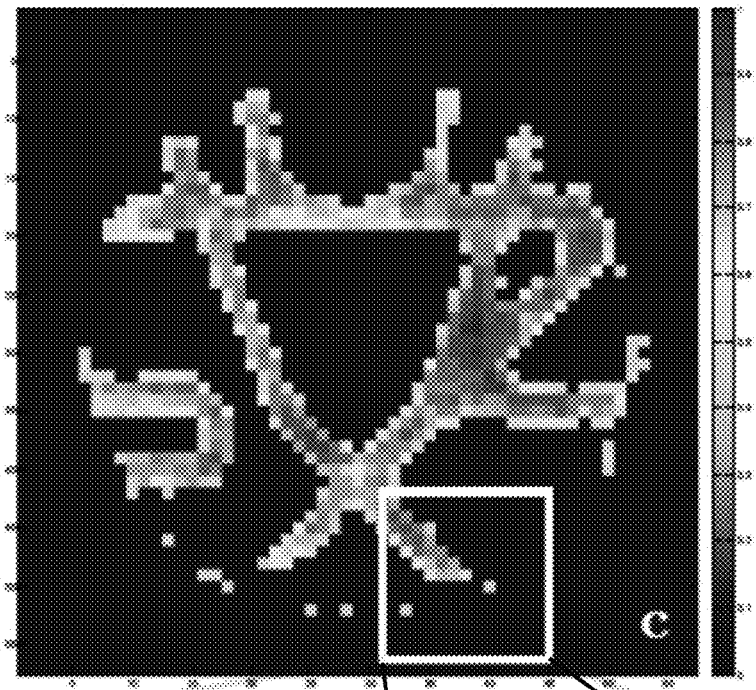
FIG. 13C is the map of equilibrium probability distribution with perfect identification of all fiber ends and overall area occupied by fiber bundles.
Figure 13F:
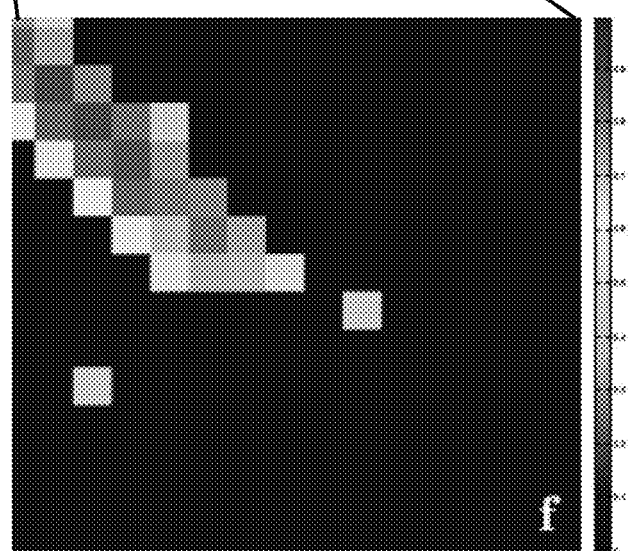

We included one of the baseline images of the fiber cup phantom in FIGS. 13A-13F (central horizontal 64×64 slice of 64×64×3 MR fiber cup phantom) to emphasize an interesting and important feature of the ESP approach. FIG. 13A illustrates one of the baseline b=0 images, with FIG. 13D providing an enlarged version of the white square area of FIG. 13A, clearly showing strong signal at the fiber end and at the circular disc interface. FIG. 13B is a map of the largest ESP transition probability values with FIG. 13E providing an enlargement of the same area showing the resolution of the fiber end. FIGS. 13C and 13F are the map of equilibrium probability distribution ($\mu^* = [\phi^{(1)}]^2$) thresholded at 0.45 with perfect identification of all fiber ends and overall area occupied by fiber bundles. The baseline image (as well as other diffusion weighted images not shown here) clearly shows bright artifacts at the interface boundaries of the disks used for phantom manufacturing. The overall effects of these artifacts are significant with the brightest spots located either at the very ends of the fiber bundles where they are cut by the disks or even at the circular boundary of the disks themselves. Thus, using simple thresholding allows identification of the ends for all of the fiber bundles. What is equally important is that ESP correctly restores the contrast that has been lost at the crossing fiber areas that can clearly be seen in $b_0$ as well as in the diffusion weighted images for different gradient directions. As previously mentioned, this helps the geometrical optics algorithm to find the correct continuation of rays in voxels with isotropic diffusion (or with many fibers of different directions crossing).

Current standard analyses that are based on the maps of the apparent diffusion coefficient (ADC) and the fractional anisotropy (FA) also favor those regions by assigning higher anisotropy and diffusion values. As a result, many of the current streamline tracing tractography approaches do not see the actual ends of the fiber bundles and continue tracts through the circular disks interfaces.

Figure 14A:
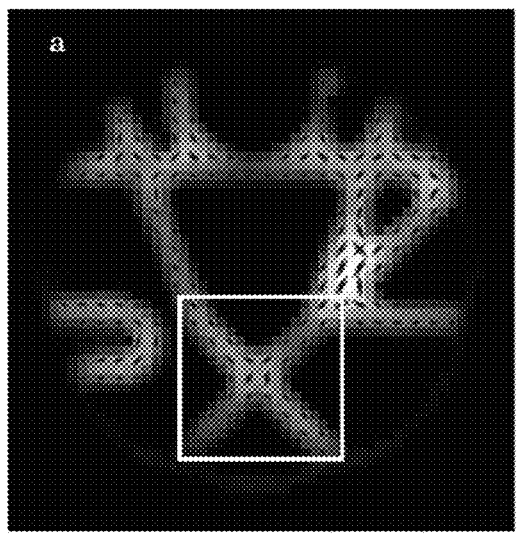
FIG. 14A illustrates local samples of different scales of transition probabilities obtained by the ESP.
Figure 14B:
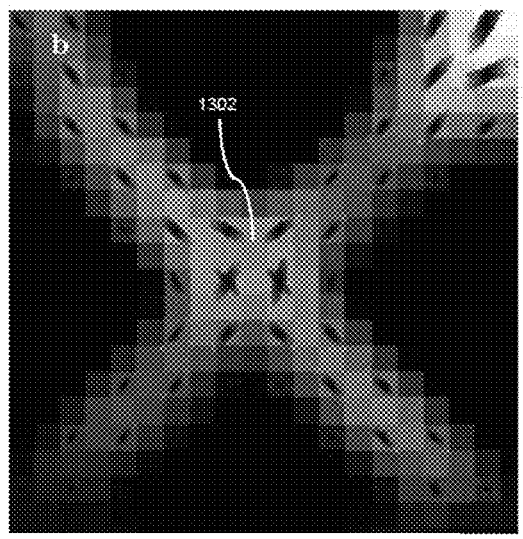
FIG. 14B is an enlargement of an area with center crossing fibers area in FIG. 14A.

The local samples of multiple scales of the transition probabilities calculated by the ESP method are presented in FIGS. 14A and 14B. The crossing fiber area 1302 illustrated in FIG. 14B, which is an enlargement of the area within the white square of FIG. 14A, clearly shows existence of different fiber directions in different scales of the transition probabilities.

To stress two important aspects of our method, first, FIGS. 14A and 14B show the multi-scale transition probabilities (as expressed by Eq. 68) rather than the EAP (or dPDF). The transition probabilities were derived not just from the local diffusion (used in EAP/dPDF). It also takes into account the nonlocal coupling between voxels by calculating the global eigenmodes and updating the probabilities according to the structure of the corresponding global eigenvectors. In this respect, the transition probabilities are more fundamental quantities than the locally derived EAPs or dPDFs.

Figure 15A:
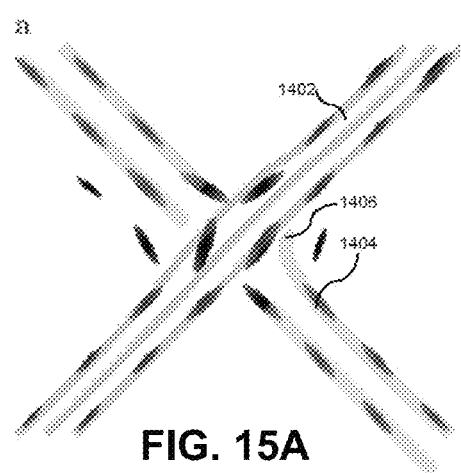
FIG. 15A schematically illustrates one possible tracking through fiber crossing area shown in FIG. 14B using only single scale transition probabilities.
Figure 15B:
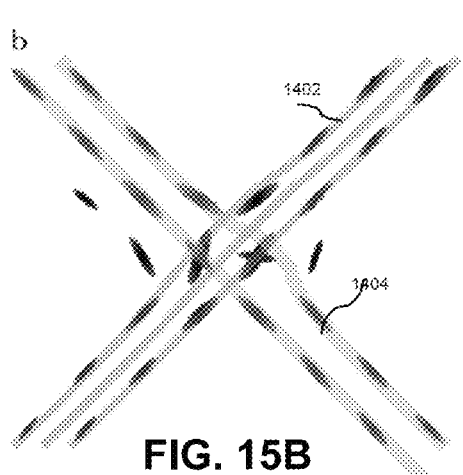
FIG. 15B shows tracking with multiple scales and coupling information used in obtaining transition probabilities.

Second, the use of multiple scales enables the geometrical optics-like approach presented here to find the correct path even when the angular resolution is relatively low. To illustrate this fact, two possible tracking scenarios are shown: FIG. 15A uses single scale transition probabilities; and FIG. 15B shows transition probabilities that include multiple scales. The single scale tracking finds only one bundle of fibers 1402, and either breaks the second set of fibers 1404 (break shown as 1406) or wrongly connects it to the first bundle. But with multiple scale transitional probabilities, the second set of fibers 1404 is found correctly with the geometrical optics-like tracking even at this relatively low angular resolution.

Figure 15C:
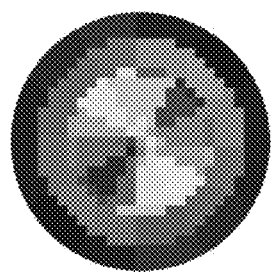
FIG. 15C is a map of EAP-like function for a single voxel from the crossing area.

Utilization of high angular resolution locally (in an isolated voxel) and without the incorporation of multiple scales and global connectivity does not necessarily guarantee detection of crossing fibers. For example, it is not possible to detect the second direction of fibers in an EAP-like function (FIG. 15C) of a single voxel from the crossing area 1302 of FIG. 14B. This EAP-like map was obtained from single voxel diffusion data using the original shell of 60 direction q-values with high angular resolution 72 mode spherical harmonics expansion. Importantly, our approach using multiscale transition probabilities and global connectivity information can identify crossings from significantly lower angular and radial resolution.

Figure 16A:
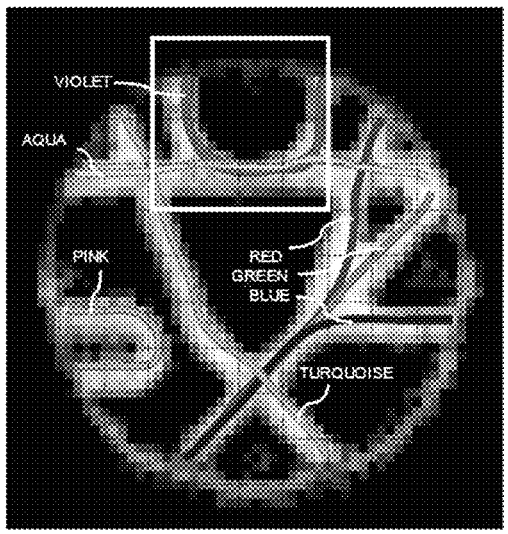
FIG. 16A illustrates several fiber tracts produced by geometrical optics ray tracing of the Fokker-Plank equation using the ESP equilibrium probability distribution of FIG. 13C.
Figure 16B:
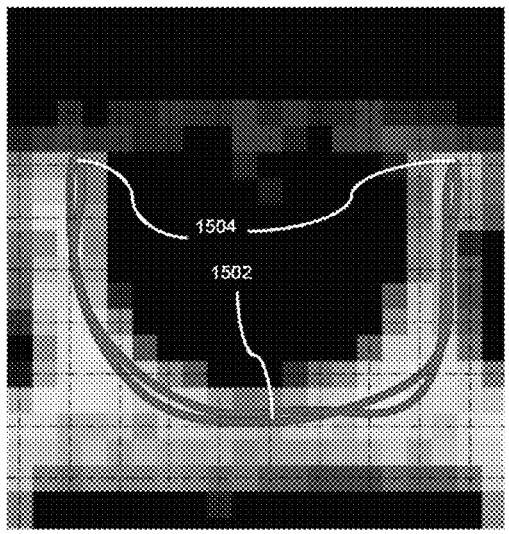
FIG. 16B is an enlarged image of one of the tracts shown in FIG. 16A.
Figure 16C:
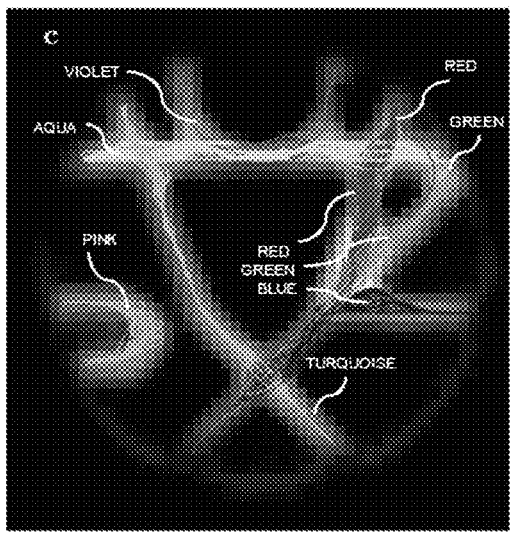
FIG. 16C shows all fiber tracts obtained using seeds shown in FIG. 16D, which were selected with single threshold from the ESP equilibrium probability distribution.

A direct comparison with the Fiber Cup results (from the 2009 Medical Image Computing and Computer Assisted Intervention (MICCAI 2009)) is illustrated in FIG. 16A. Several possible fiber tracts obtained by integrating the equations of geometrical optics rays for Fokker-Plank formalism (Eqs. 81 and 82) are displayed. The phantom includes several different types of fiber crossings (at different angles), as well as kissings and splits/joints. To illustrate one peculiar feature of the approach based on geometrical optics we included the blow up of one of the fiber tracts. In the boundary area where the underlying fibers end abruptly, the ray tracing algorithm may produce a reflection of the ray from the interface and proceed following the same (or neighboring) fiber backwards. In FIG. 16B, which is an enlargement of the upper area in the white box of FIG. 16A, showing only the violet fiber tract, the reflection happens at two ends 1504 of the fiber 1502 and results in a closed horseshoe-like loop that is being traversed back and forth many times. Of course, we included this close-loop tract only as an example as identifying the reflection regions and cutting the fibers at these points instead of reflecting would be a fairly easy task.

Figure 16D:
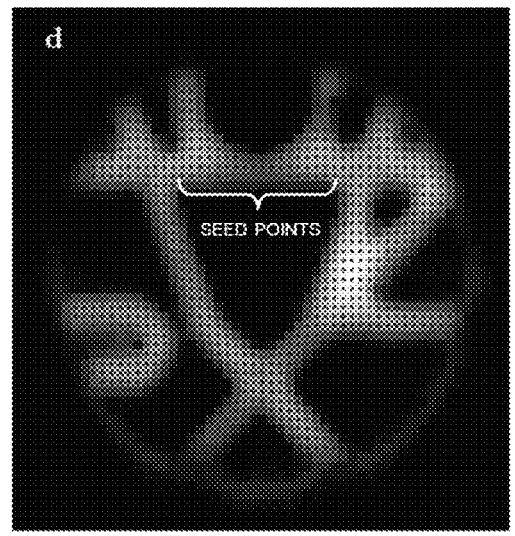

To generate fiber tracts we selected seed points, illustrated by blue dots in FIG. 16D, by thresholding the map of the ESP equilibrium probabilities. Using all 512 selected seed points, the algorithm produced 372 total fiber tracts. All but two fiber tracts are topologically equivalent to one of the seven tracts shown in FIG. 16A, which are labeled as "VIOLET", "AQUA", "PINK", "RED", "GREEN", "BLUE", and "TURQUOISE". Two fiber tracts (RED and GREEN) show the end points switched. These two incorrect tracts yield 0.5% false positive error rate. In general, simple post processing can remove even those two outliers using, for example, the total fiber tract length or the distinct change in the fiber curvature as a source of discrimination. In addition, all of the fibers can be evaluated using, for example, Tracktometer, the tractography evaluation software available on the World Wide Web from the Sherbrook Connectivity Imaging Laboratory (SCIL). Our motivation for using the Fiber Cup data was precisely because it facilitates comparison of our results with previously published results. Further detailed analysis on a phantom that has a rather limited connection to human brain data is ultimately of little importance.

For human brain ESP tractography we collected multi b-shell multi q-angle DWI dataset on the GE MR750 3T scanner at the UCSD Center for FMRI using a multi-band blipped-CAIPI EPI method with a GRAPPA reconstruction. Each data set was collected with both forward and reversed phase encoding polarity in order to perform a "topup" distortion and eddy current correction using FSL. The dataset contains three shells at b=1000, 2000 and 3000 s/mm$^2$. Each b-shell uses different number of q-values, with 30 angles for b=1000 s/mm$^2$, 45 angles for b=2000 s/mm$^2$, and the largest at 60 angles for b=3000 s/mm$^2$.

Figure 17:
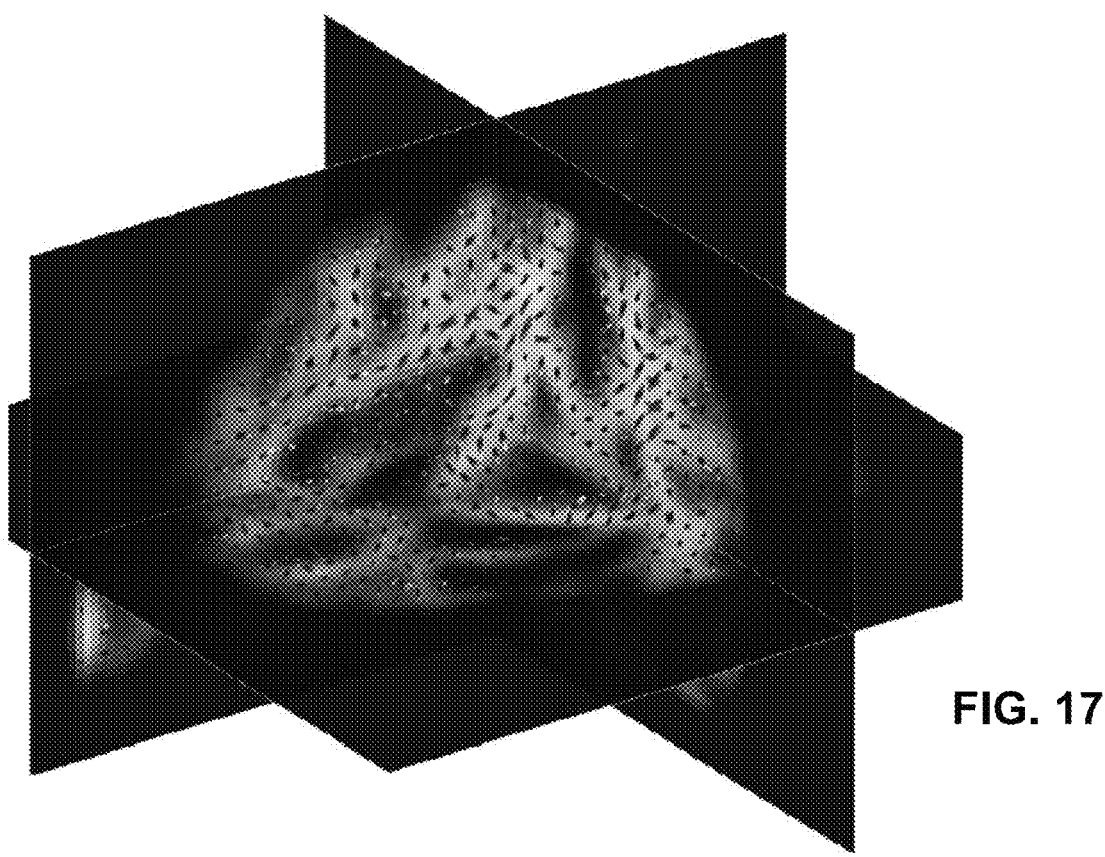
FIG. 17 shows different slices of three dimensional equilibrium probabilities obtained using diffusion weighted images of human brain with local samples of different scales of transition probabilities shown by directionally colored ellipsoids.

Several slices of three dimensional eigenvector map obtained by the ESP solution are shown in FIG. 17. The local samples of transition probabilities are shown by directionally colored ellipsoids, which represent the diffusion in each voxel. The multi-scale structure of the ESP approach can be used for identifying fiber crossings—it can be seen clearly in many of these samples that different scales show different main fiber direction.

Figure 18A:
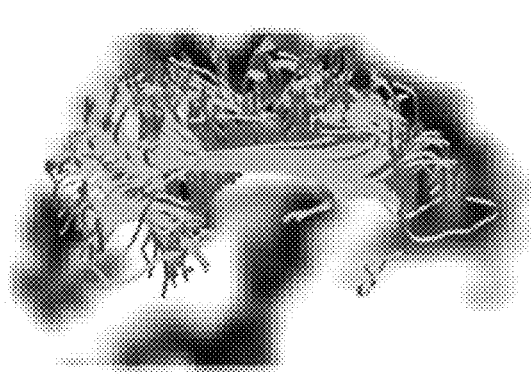
FIGS. 18A-18F illustrate examples of fiber tracts obtained by geometrical optics-like processing of ESP guided tractography, with ESP equilibrium probability distribution shown by grayish transparent background.
Figure 18B:
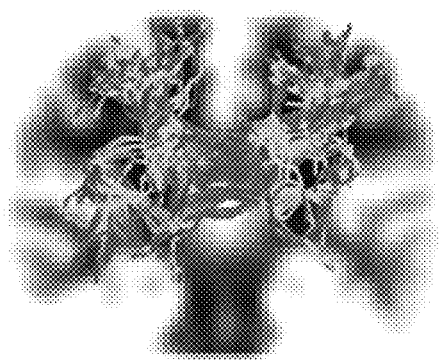
Figure 18C:
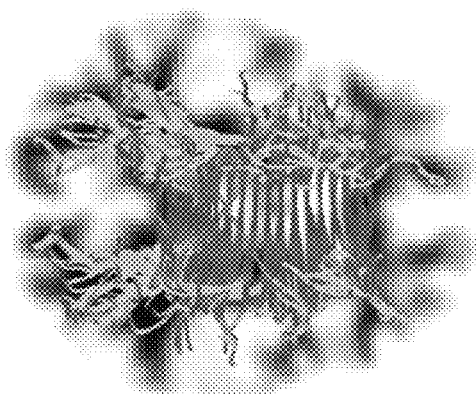
Figure 18D:
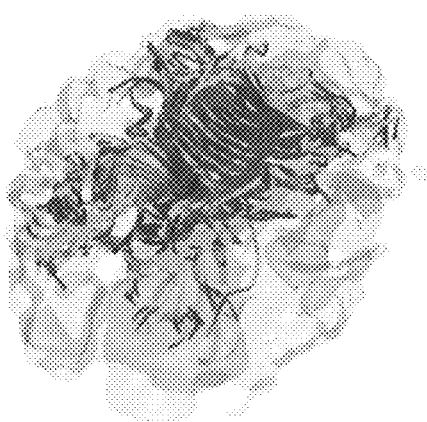
Figure 18E:
Figure 18F:
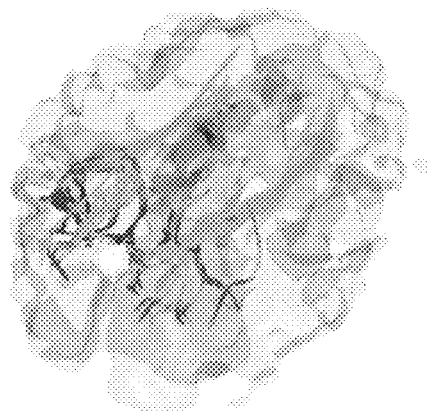
Figure 19A:
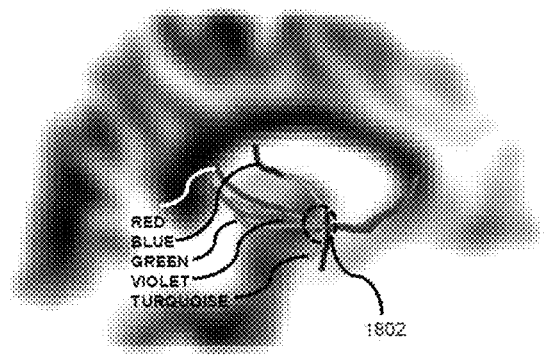
FIGS. 19A-19C are coronal, sagittal and axial planes showing five fiber tracts going through a small region where a mixture of different fiber orientations emphasizes different directions at different scales.
Figure 19B:
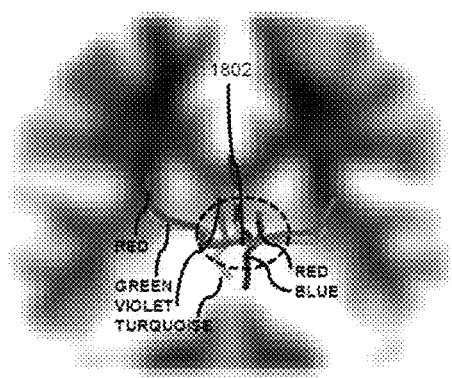
Figure 19C:
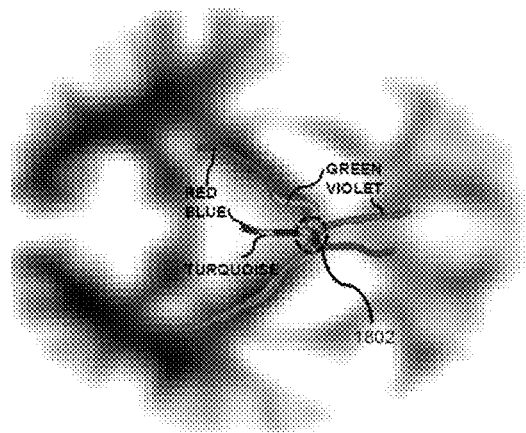
Figure 19D:
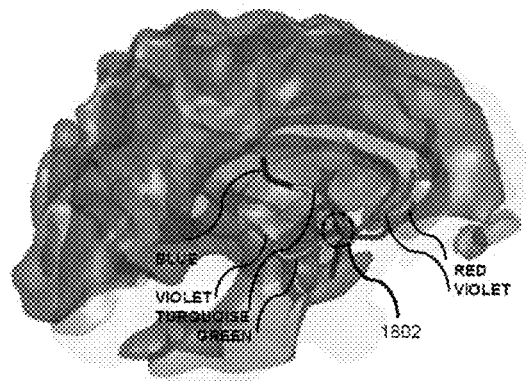
FIG. 19D shows a 3D view.
Figure 20A:
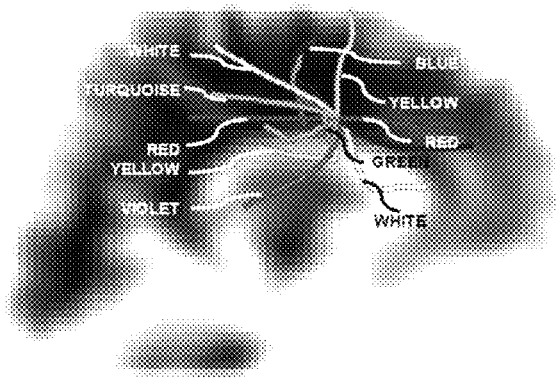
FIGS. 20A-20C are coronal, sagittal and axial planes showing seven fiber tracts with the same single voxel seed located in the area where the corticospinal tract crosses the corpus callosum.
Figure 20B:
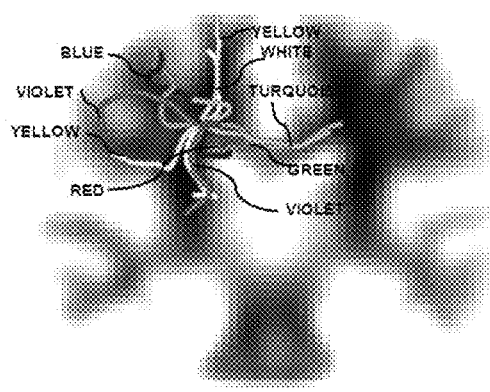
Figure 20C:
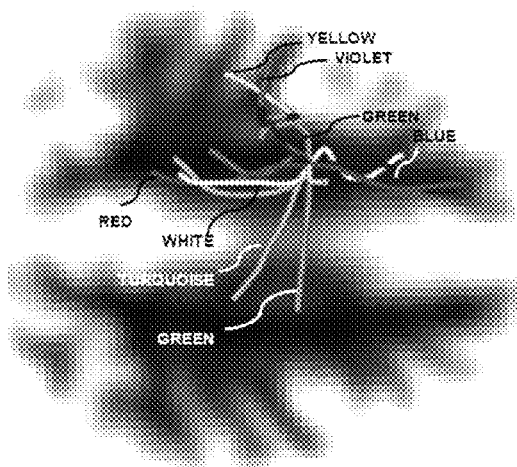
Figure 20D:
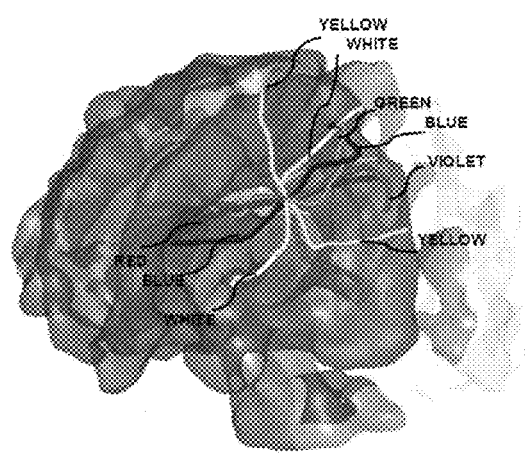
FIG. 20D is a 3D view.

To illustrate the practical ability of geometrical optics-like tracking of fibers though those "difficult" areas of multiple fibers with different orientations we generated fiber tracts for several sets of seed points located in the areas of corpus callosum and longitudinal fasciculus that are known to have multiple overlaps in both inferior and fronto-occipital regions. FIGS. 18A-18F illustrate examples of fiber tracts obtained by geometrical optics-like processing of ESP guided tractography, with ESP equilibrium probability distribution shown by grayish transparent background. The 135 corpus callosum seed points were grouped in blocks of three consecutive voxels coronally and two or three voxels vertically. In the fasciculus region two sets of seeds were selected in left and right hemispheres with 30 seeds each again grouped in blocks by three consecutive voxels vertically and five consecutive voxels coronally. The total number of seeds were 195 voxels resulting in 195 distinct fiber tracts. FIGS. 18A-18D correspond to different projections (coronal, sagittal and axial planes, and 3D perspective, respectively) and FIGS. 18E and 18F are perspective views showing tracts with seeds in corpus callosum and fasciculus, respectively. The corpus callosum originating fibers and fibers going through longitudinal fasciculus are crossing in areas occupying multiple voxels and the ESP tractography with geometrical optics-like tracking is able to correctly proceed through those voxels.

The seeds were selected primarily in the regions with predominantly single fiber orientation. Using the multiscale ESP-guided geometrical optics-like approach, the tracking algorithm is able to continue tracts across voxels with a mixture of fibers of different orientations and select the correct path based on the combination of local and global parameters.

For a more "difficult" starting point, we first chose several seed voxels in the area around the splenium of the corpus callosum and up to the internal capsule. The five fiber tracts, shown in FIGS. 19A-19D, labeled according to colors ("RED", "BLUE", "GREEN", "VIOLET", and "TURQUOISE") clearly cross a rather small area 1802 into different directions, ranging from a latero-lateral (left to right and right to left) to an anterior-posterior and to a dorsal-ventral. This example shows that the multiple scales used by ESP guided geometrical optics-like approach can help resolve crossing of multiple fibers in a small area of only several voxels extent.

To study behavior of our approach in even more difficult conditions, we selected a single seed voxel that is located into a region where the corticospinal tract crosses the corpus callosum. This is a region that is well known for crossing fiber problems, and appears often in the DTI literature. Even starting with just a single voxel seed in the "difficult" area, the multiscale multi-modal approach is able to find and distinguish several fibers that go into different regions of brain shown in FIGS. 20A-20D. Seven fiber tracts are labeled according to color: "RED", "BLUE", "GREEN", "TURQUOISE", "YELLOW", "VIOLET" and "WHITE." The fiber tract labeled "WHITE", which would be produced by a standard tractography approach with a single scale integration of the principal direction of the diffusion tensor, is included for comparison.

Figure 21A:
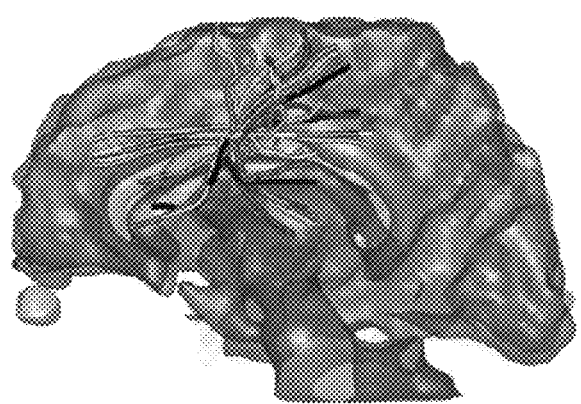
FIGS. 21A-21C are coronal, sagittal and axial planes showing several bundles of fiber tracts obtained when seeded by several voxels in the vicinity of a single seed voxel used in FIGS. 20A-20D.
Figure 21B:
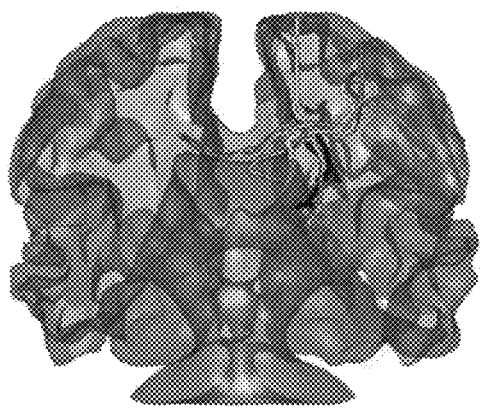
Figure 21C:
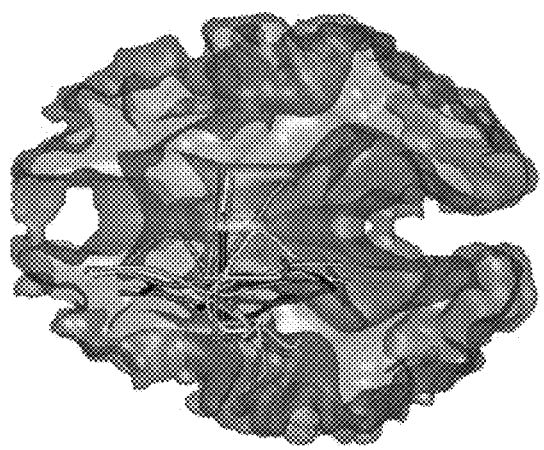
Figure 21D:
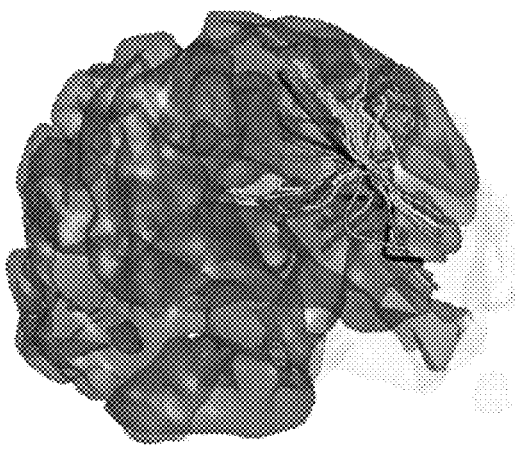
FIG. 21D is a 3D view.
Figure 21E:
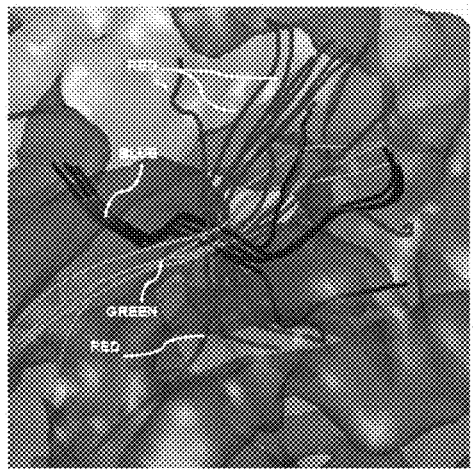
FIGS. 21E and 21F show different projections of a zoomed area with fibers grouped according to type.
Figure 21F:
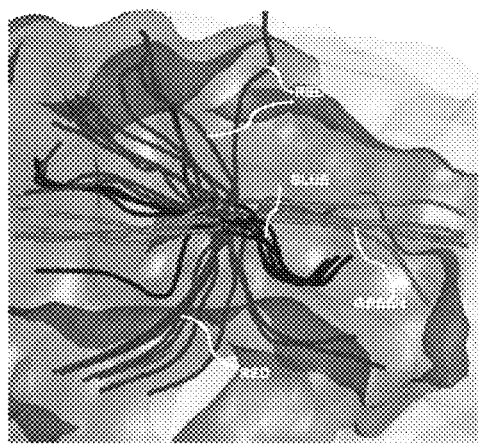

Using several seeds in the small vicinity of the single seed voxel used in FIGS. 20A-20D gives more complicated behavior with a bundle of fibers going in and out of the corpus callosum, a bundle coming to/from the corticospinal tract, a bundle connecting anterior posterior regions, and some bundles going to outer regions of the brain. FIGS. 21A-21C show coronal, sagittal and axial planes, respectively. FIG. 21D shows a 3D view of the same region. FIGS. 21E and 21F show different projections of zoomed area with fibers grouped in (a) going from/to the corpus callosum (labeled "BLUE"), (b) coming to/from the corticospinal tract ("RED") and (c) longitudinal fibers ("GREEN").

The inventive approach is a novel diffusion estimation and fiber tractography method that is based on simultaneous estimation of global and local parameters of neural tracts from maximum entropy principles and sorting them into a series of entropy spectral pathways (ESP). The method uses local coupling between sub-scale diffusion parameters to compute the structure of the equilibrium probabilities that define the global information entropy field and uses this global entropy to update the local properties of neural fiber tracts.

In some embodiments, the method provides an efficient way to trace individual tracts using the multi-scale and multi-modal structure of the local diffusion-convection propagation by means of an approach reminiscent of the geometrical optics ray tracing in dispersive media (either elastic or viscoelastic). This geometrical optics-like approach naturally includes multiple scales that allow fiber tracing to continue fibers through voxels with complex local diffusion properties where multiple fiber directions are unable to be adequately resolved.

One of the most important aspects of the inventive method is that it is "global" in the sense that data from spatially extended brain structures are being used to inform both the local diffusion and generation of tracts. The typical workflow of the majority of other global algorithms used in tractography, including algorithms based on the well-known shortest-path algorithm on graphs by Dijkstra, represent the brain as a graph, where each voxel is a node, in which they have a local estimation of the diffusion process that they use as a speed function to guide a front evolution evolving from a seed point. Then, the geodesic or shortest-path between this point and any other location in the brain can be easily computed with backtracking. While there might appear to be similarities with the inventive method, we point out that both the theoretical foundations and the numerical implementation for our approach are quite different from these schemes. Our method does not represent the brain as a graph—it only uses nearest neighbors input in the coupling. The local estimation of the diffusion process is not used as a speed function. Rather, the prior coupling is used to find the global eigenvalues/vectors, rank those information pathways based on a maximum entropy, and spread this global information about pathways to every voxel. The global information used in every voxel is more than an analog of a locally inferred speed function—it is more akin to a dispersion of fibers. For each voxel this function includes both angular and radial (scale) distributions obtained as a collective effect of all fibers that cross in a single voxel.

The disclosed tracking process, although it might appear to be a front evolution, is not. The inventive approach does not need an explicit front evolution step at all. The eigensystem calculation of the connectivity matrix provides more complete and accurate path information than is available from the typical front evolution methods, and does it more efficiently. The inventive tracking is performed in 6-dimensional coordinate and momentum space. Not only is the position of each fiber updated on each step, but a momentum equation is used to update the local fiber orientation as well as a rate of orientation change based on a globally constructed distribution/dispersion of fibers. All the current tracking algorithms, including the shortest-path algorithms, only update a position of fiber assuming its orientation defined by static (fixed at each voxel position) speed function.

It is important to reiterate that the inventive method formulates the analysis problem as one of inference where the goal is to make the most accurate estimates of both the local diffusion and the extended fiber tracts based only upon the available data and any relevant prior information. This approach is based on the logic of probability theory: the theoretical basis for the method is a probabilistic analysis of information flow in a lattice.

A key conclusion that can be drawn using the methods disclosed herein is that local coupling information provides significant information about global pathways, which thus forms the important connection between local phenomena (diffusion) and global structures (fiber tracts). In addition, the dynamics of how local effects inform global structures can be characterized by a Fokker-Planck equation with a potential equal to the entropy, a formulation that had previously been put forth in a general theoretical framework, but here finds a very practical manifestation, as it facilitates a geometric-optics tractography scheme where the relationship between the local diffusion measurements and the global fiber tract structure is made explicit.

An important point demonstrated by the inventive method is that the connection between the local and the global properties of the diffusion field are mediated by the transition probability, which emerges as a more fundamental quantity than the traditional diffusion PDF (probability density function). In effect, the inventive approach makes explicit a fact that is often implicitly assumed in diffusion analysis papers but rarely explicitly addressed: There is a fundamental logical flaw in estimating the local diffusion as if it were taking place in independent, isolated voxels, but then using it to generate connections between voxels based on their assumed dependence. Our formulation naturally incorporates the continuum of spatial scales, from local to global, and avoids unnecessary arguments related to the fact that the actual diffusion is occurring on a scale much smaller than the measurement process, and thus far smaller than the scale of the fiber structures, since we are only requiring that our macroscopic predictions from microscopic phenomena are consistent with our data and prior information.

The computer-implemented method for fiber tractography based on Entropy Spectrum Pathways includes instructions fixed in a computer-readable medium that cause a computer processor to solve an eigenvector problem for the probability distribution and use it for an integration of the probability conservation through ray tracing of the convective modes guided by a global structure of the entropy spectrum coupled with a small scale local diffusion. The intervoxel diffusion is sample by multi b-shell multi q-angle DWI data expanded in spherical harmonics and spherical Bessel series.

According to embodiments of the invention, the problem of local diffusion estimation and fiber tractography is addressed with the specific goal of including multiple spatial and temporal scales that can be deduced from multiple b-shell DW-MRI measurements in addition to just angular (multi-)fiber orientation. In many practical applications, either one or two spatial locations (or regions) are known a priori. In neuroscience applications, for example, two regions may be functionally connected (as measured, perhaps, by FMRI) and the diffusion weighted MRI data is being used to assess the degree (if any) of the structural connectivity between two functionally connected regions. We therefore reconsider two common formulations of fiber tractography: (1)—initial value, i.e. finding fibers that start at some chosen area of the brain, (2)—boundary value, i.e. finding fibers that connect two preselected brain regions. Thus we recast the fiber tractography algorithm as the determination of the most probable path either starting at a selected location or connecting two spatial locations, and seek a general probabilistic framework that can accommodate various local diffusion models and yet can incorporate the structure of extended pathways into the inference process. In this case, the problem of tractography from DWI data can be reformulated as the determination of the probability of paths on a 3D lattice between two given points where the probability of a path passing through any particular point is not equiprobable, but is weighted according to the locally measured diffusion characteristics.

Applications of the ESP method include any commercial neuroscience application involved in the quantification of connectivity, including neural fiber connectivity using diffusion tensor imaging, functional connectivity using functional MRI, or anatomical connectivity using segmentation analysis. The ESP method may also be used as a tool for characterization of connectivity in networks, examples of which include the internet and communications systems.

REFERENCES (INCORPORATED HEREIN BY REFERENCE)

[1] S. Mori, et al., "Three-dimensional tracking of axonal projections in the brain by magnetic resonance imaging." *Ann. Neural.*, vol. 45, no. 2, pp. 265-269, February 1999.

[2] T. Conturo, et al., "Tracking neuronal fiber pathways in the living human brain." *Proc. Natl. Acad. Sci. USA*, vol. 96, pp. 10422-10427, August 1999.

[3] P. Basser, et al., "In vivo fiber tractography using (DT MRI) data," *Magn. Reson. Med.*, vol. 44, pp. 625-632, 2000.

[4] T. Behrens, et al., "Probabilistic diffusion tractography with multiple fibre orientations: What can we gain?" *Neuroimage*, vol. 34, no. 1, pp. 144-155, 2007.

[5] D. Jones, "Tractography gone wild: probabilistic fibre tracking using the wild bootstrap with diffusion tensor MRI," *Medical Imaging, IEEE Transactions on*, vol. 27, no. 9, pp. 1268-1274, 2008.

[6] M. Descoteaux, et al., "Deterministic and probabilistic tractography based on complex fibre orientation distributions," *Medical Imaging, IEEE Transactions on*, vol. 28, no. 2, pp. 269-286, 2009.

[7] N. Ratnarajah, et al., "Novel Approach for Improved Tractography and Quantitative Analysis of Probabilistic Fibre Tracking Curves," *Medical Image Analysis Journal*, 2011.

[8] S. Jbabdi, et al., "A Bayesian framework for global tractography," Neuroimage, vol. 37, no. 1, pp. 116-129, August 2007.

[9] I. Aganj, et al., "A Hough transform global probabilistic approach to multiple-subject diffusion MRI tractography," *Medical Image Analysis*, 2011.

[10] J. Mangin, et al., "A framework based on spin glass models for the inference of anatomical connectivity from diffusion weighted MR data—a technical review," *NMR in Biomedicine*, vol. 15, no. 78, pp. 481-492, 2002.

[11] B. Kreher, et al., "Gibbs tracking a novel approach for the reconstruction of neuronal pathways," *Magnetic Resonance in Medicine*, vol. 60, no. 4, pp. 953-963, 2008.

[12] P. Pillard, et al., "A novel global tractography algorithm based on an adaptive spin glass model," Medical Image Computing and Computer-Assisted Intervention—MICCAI 2009, pp. 927-934, 2009.

[13] M. Reisert, et al., "Global fiber reconstruction becomes practical," *Neuroimage*, vol. 54, no. 2, pp. 955-962, 2011.

[14] P. Basser and C. Pierpaoli, "Microstructural and physiological features of tissues elucidated by quantitative diffusion tensor MRI." *J. Magn. Reson. B.*, vol. 111, pp. 209-219, 1996.

[15] S. Farquharson, et al., "White matter fiber tractography: why we need to move beyond DTI," *J. Neurosurg.*, vol. 118, no. 6, pp. 1367-1377, June 2013.

[16] D. Tuch, et al., "High angular resolution diffusion imaging reveals intravoxel white matter fiber heterogeneity." *Magn. Reson. Med.*, vol. 48, pp. 577-582, 2002.

[17] P. J. Basser, et al., "MR diffusion tensor spectroscopy and imaging," *Biophys. J.*, vol. 66, no. 1, pp. 259-267, January 1994.

[18] D. S. Tuch, "Q-ball imaging," *Magn Reson Med*, vol. 52, no. 6, pp. 1358-1372, December 2004.

[19] L. Frank, "Characterization of anisotropy in high angular resolution diffusion weighted MRI." *Magn Reson Med*, vol. 47, no. 6, pp. 1083-1099, June 2002.

[20] E. Ozarslan and T. Mareci, "Generalized diffusion tensor imaging and analytical relationships between diffusion tensor imaging and high angular resolution diffusion imaging," *Magn. Reson. Med.*, vol. 50, no. 5, pp. 955-965, 2003.

[21] A. Anderson, "Measurement of fiber orientation distribution s using high angular resolution diffusion imaging," *Magnetic Reson. Med.*, vol. 54, no. 5, pp. 1194-1206, 2005.

[22] M. Descoteaux, et al., "Apparent diffusion coefficients from high angular resolution diffusion imaging: Estimation and applications," *Magnetic Reson. Med.*, vol. 56, no. 2, pp. 395-410, 2006.

[23] F. C. Yeh, et al., "Generalized q-sampling imaging," *IEEE Trans Med Imaging*, vol. 29, no. 9, pp. 1626-1635, September 2010.

[24] V. J. Wedeen, et al., "Mapping complex tissue architecture with diffusion spectrum magnetic resonance imaging," *Magn Reson Med.*, vol. 54, no. 6, pp. 1377-1386, December 2005.

[25] M. Descoteaux, et al., "Multiple q-shell diffusion propagator imaging," *Med Image Anal*, vol. 15, no. 4, pp. 603-621, August 2011.

[26] S. L. Merlet and R. Deriche, "Continuous diffusion signal, EAP and ODF estimation via Compressive Sensing in diffusion MRI," *Med Image Anal*, vol. 17, no. 5, pp. 556-572, July 2013.

[27] A. P. Hosseinbor, et al., "Bessel Fourier Orientation Reconstruction (BFOR): an analytical diffusion propagator reconstruction for hybrid diffusion imaging and computation of q-space indices," *Neuroimage*, vol. 64, pp. 650-670, January 2013.

[28] N. S. White, et al., "Probing tissue microstructure with restriction spectrum imaging: Histological and theoretical validation," *Hum Brain Mapp*, vol. 34, no. 2, pp. 327-346, February 2013.

[29] D. Cory and A. Garroway, "Measurement of translational displacement probabilities by NMR: An indicator of compartmentation." *Magn Res Med*, vol. 14, p. 435, 1990.

[30] P. T. Callaghan, *Principles of nuclear magnetic resonance microscopy*, Oxford University Press, 1993.

[31] G. B. Tefera, et al., "Evaluation of fiber tracking from subsampled q-space data in diffusion spectrum imaging," *Magn Reson Imaging*, vol. 31, no. 6, pp. 820-826, July 2013.

[32] S. B. Vos, et al., "Multi-fiber tractography visualizations for diffusion MRI data," *PLoS ONE*, vol. 8, no. 11, p. e81453, 2013.

[33] S. Jbabdi, et al., "Model-based analysis of multi shell diffusion MR data for tractography: how to get over fitting problems," *Magn Reson Med*, vol. 68, no. 6, pp. 1846-1855, December 2012.

[34] L. R. Frank and V. L. Galinsky, "Information pathways in a disordered lattice," *Phys. Rev. E*, vol. 89, p. 032142, March 2014.

[35] V. L. Galinsky and L. R. Frank, "Automated Segmentation and Shape Characterization of Volumetric Data," *Neuroimage*, 92:156-168, May 2014.

[36] N. Lebedev, *Special functions and their applications*. Revised edition, translated from the Russian and edited by Richard A. Silverman. Unabridged and corrected republication. Dover Publications, Inc., New York, 1972.

[37] Y. A. Kravtsov and Y. I. Orlov, *Geometrical Optics of Inhomogeneous Media*. Berlin: Springer-Verlag, 1990.

[38] E. Ozarslan, et al., "Temporal scaling characteristics of diffusion as a new MRI contrast: findings in rat hippocampus," *Neuroimage*, vol. 60, no. 2, pp. 1380-1393, April 2012.

[39] E. Ozarslan, et al. "Resolution of complex tissue microarchitecture using the diffusion orientation transform (DOT)," *Neuroimage*, vol. 3 1, no. 3, pp. 1086-1103, July 2006.

[40] Z. Burda, et al., "Localization of the maximal entropy random walk," *Phys. Rev. Lett.*, vol. 102, no. 16, p. 160602, 2009.

[41] Z. Burda, et al., "The various facets of random walk entropy," *Acta Phys. Polon. B* 41, 949 (2010), arXiv: J004.3667.

[42] C. Shannon, "A mathematical theory of communication," *Bell Syst. Tech. J.*, vol. 27, pp. 379423, 623656, 1948.

[43] B. McMillan, "The basic theorems of information theory," *Ann. Math. Stat.*, vol. 24, no. 2, pp. 196-219, 1953.

[44] H. Grabert and M. Green, "Fluctuations and nonlinear irreversible processes," *Physical Review A*, vol. 19, no. 4, pp. 1747-1756, April 1979.

[45] E. Jaynes, "Macroscopic prediction," in *Complex Systems—Operational App roaches in Neurobiology, Physics, and Computers*, H. Haken, Ed. Berlin: Springer-Verlag, 1985, pp. 254-269.

[46] P. D. Lax, "A symptotic solution s of oscillatory initial value problems," *Duke Mathematical Journal*, vol. 24, no. 4, pp. 627-646, 12 1957.

[47] P. Pillard, et al., "Quantitative evaluation of 10 tractography algorithms on a realistic diffusion MR phantom," *Neuroimage*, vol. 56, no. 1, pp. 220-234, May 2011.

[48] M.-A. Cote, et al., "Tractometer: Towards validation of tractography pipelines," *Medical Image Analysis*, vol. 17, no. 7, pp. 844-857, 2013.

[49] K. Setsompop, et al., "Blipped-controlled aliasing in parallel imaging for simultaneous multislice echo planar imaging with reduced g-factor penalty," *Magn Res Med*, vol. 67, no. 5, pp. 1210-1224, August 2011.

[50] M. A. Griswold, et al., "Generalized autocalibrating partially parallel acquisitions (GRAPPA)," *Magn Res Med*, vol. 47, no. 6, pp. 1202-1210, June 2002.

[51] J. L. R. Andersson, et al. "How to correct susceptibility distortions in spin-echo echo-planar images: application to diffusion tensor imaging," *Neuroimage*, vol. 20, no. 2, pp. 870-888, October 2003.

[52] S. M. Smith, et al., "Advances in functional and structural MR image analysis and implementation as FSL," *Neuroimage*, vol. 23, pp. S208-S219, January 2004.

[53] M. Catani, et al., "A diffusion tensor imaging tractography atlas for virtual in vivo dissections," *Cortex*, vol. 44, no. 8, pp. 1105-1132, September 2008.

[54] E. Dijkstra, "A note on two problems in connexion with graphs," *Numerische Mathematik*, vol. 1, no. 1, pp. 269-271, 1959.

[55] G. J. Parker, et al., "Estimating distributed anatomical connectivity using fast marching methods and diffusion tensor imaging," *IEEE Trans Med Imaging*, vol. 21, no. 5, pp. 505-512, May 2002.

[56] S. Jbabdi, et al., "Accurate anisotropic fast marching for diffusion-based geodesic tractography," *Int J Biomed Imaging*, vol. 2008, p. 320195, 2008.

[57] A. Zalesky, "DT-MRI fiber tracking a shortest path s approach," *IEEE Trans Med Imaging*, vol. 27, no. 10, pp. 1458-1471, October 2008.

[58] E. Jaynes, *Probability Theory: The Logic of Science*. New York: Cambridge University Press, 2003.

The invention claimed is:

1. A method for fiber tractography, comprising:
acquiring, via an imaging system, diffusion weighted MRI data comprising a plurality of voxels, wherein the plurality of voxels defines a lattice, each voxel connected by a path;
inputting the MRI data into a computer processor having instructions stored therein for causing the computer processor to execute the steps of:
calculating intravoxel diffusion characteristics from the MRI data;
calculating a transition probability for each path on the lattice, wherein the transition probability is weighted according the intravoxel characteristics;
calculating an entropy for each path;
ranking the paths between two voxels according to entropy to determine a maximum entropy;
calculating a connection between a global structure of the probability with a local structure of the lattice by applying the Fokker-Planck equation to one or more highest ranked paths, wherein potential equals entropy;
calculating a location and direction of one or more fiber tracts by applying geometric optics algorithms to the results of the Fokker-Planck equation; and
generating an output comprising a display corresponding to the one or more fiber tracts.

2. The method of claim 1, wherein the Fokker-Planck equation is $$\partial_t P + \nabla \cdot (LP\nabla S) = \nabla \cdot D\nabla P,$$

where P is probability=$P_0+P_1$, S is the entropy, D is a diffusion coefficient, and L is a local diffusion tensor, where L=$\kappa$D, where $\kappa$ is the Onsager coefficient.

3. The method of claim 1, where the geometric optics algorithms comprise $$\frac{dr}{dt} = \frac{2}{V_R} \int [X(k \cdot X) + 2kY(Y|k|^2 - Z)] dR \text{ and}$$

$$\frac{dk}{dt} = -\frac{2}{V_R} \int [(k \cdot X)\nabla(k \cdot X) + (|k|^2 Y - Z)(|k|^2 \nabla Y - \nabla Z)] dR,$$

where r is the location, R is displacement, k is the direction, t is time, $X=\nabla P_0(2+\ln P_0)+\nabla(P_0(1+\ln P_0))$, $Y=P_0(1+\ln P_0)$, and $Z=\nabla \cdot \nabla P_0(2+\ln P_0)$.

4. A method for fiber tractography, comprising:
acquiring, via an imaging system, diffusion weighted MRI data comprising a plurality of voxels, wherein the plurality of voxels defines a lattice, each voxel connected by a path;
inputting the MRI data into a computer processor having instructions stored therein for causing the computer processor to execute the steps of:

calculating intravoxel diffusion characteristics from the MRI data;

calculating a transition probability for each path on the lattice, wherein the transition probability is weighted according the intravoxel characteristics;

calculating an entropy for each path;

ranking the paths between two voxels according to entropy to determine a maximum entropy;

calculating a connection between a global structure of the probability with a local structure of the lattice for one or more highest ranked paths;

determining one or more fiber tracts corresponding to the highest ranked paths using ray tracing, wherein potential equals entropy; and generating an output comprising a display corresponding to the one or more fiber tracts.

5. The method of claim 4, wherein calculating a connection comprises applying the relationship $\partial_t P + \nabla \cdot (LP\nabla S) = \nabla \cdot D \nabla P$ to the one or more highest ranked paths, where P is probability=$P_0+P_1$, S is the entropy, D is a diffusion coefficient, and L is a local diffusion tensor, where L=$\kappa$, where $\kappa$ is the Onsager coefficient.

6. The method of claim 4, wherein ray tracing comprising applying geometric optics algorithms to the highest ranked paths according to the relationships $$\frac{dr}{dt} = \frac{2}{V_R} \int [X(k \cdot X) + 2kY(Y|k|^2 - Z)] dR \text{ and}$$

$$\frac{dk}{dt} = -\frac{2}{V_R} \int [(k \cdot X)\nabla(k \cdot X) + (|k|^2 Y - Z)(|k|^2 \nabla Y - \nabla Z)] dR,$$

where r is the location, R is displacement, k is the direction, t is time, X=$\nabla P_0(2+\ln P_0)+\nabla(P_0(1+\ln P_0))$, Y=$P_0(1+\ln P_0)$, and Z=$\nabla \cdot \nabla P_0(2+\ln P_0)$.

7. A method for fiber tractography, comprising:

acquiring, via an imaging system, multi-shell diffusion weighted MRI data comprising a plurality of voxels, wherein the plurality of voxels define locations on a lattice, each location connected by a path;

in a computing device, executing the steps of:

performing a spherical wave decomposition on the data to define a set of spherical wave decomposition coefficients;

using the spherical wave decomposition coefficients, generating a coupling matrix for diffusion connectivity at multiple scales, wherein the coupling matrix defines interactions between locations on the lattice;

using the coupling matrix, computing transition probabilities and equilibrium probabilities for a plurality of interactions between locations on the lattice;

using the computed transition probabilities to represent angular and scale distributions of potential paths between locations on the lattice;

applying a geometric optics tractography algorithm to the transition probabilities to construct possible pathways, each possible pathway having an eigenvector and an eigenvalue;

calculating eigenmodes for the possible pathways;

ranking the possible pathways according to their eigenmode;

defining a preselected number of pathways from the ranked pathways; and displaying the preselected number of pathways on a visual display.

8. The method of claim 7, wherein using the computed transition probabilities comprises applying the relationship $\partial_t P + \nabla \cdot (LP\nabla S) = \nabla \cdot D \nabla P$ to the one or more highest ranked paths, where P is probability=$P_0-P_1$, S is the entropy, D is a diffusion coefficient, and L is a local diffusion tensor, where L=$\kappa D$, where $\kappa$ is the Onsager coefficient.

9. The method of claim 7, wherein the geometric optics tractography algorithm comprises $$\frac{dr}{dt} = \frac{2}{V_R} \int [X(k \cdot X) + 2kY(Y|k|^2 - Z)] dR \text{ and}$$

$$\frac{dk}{dt} = -\frac{2}{V_R} \int [(k \cdot X)\nabla(k \cdot X) + (|k|^2 Y - Z)(|k|^2 \nabla Y - \nabla Z)] dR,$$

where r is the location, R is displacement, k is the direction, t is time, X=$\nabla P_0(2+\ln P_0)+\nabla(P_0(1+\ln P_0))$, Y=$P_0(1+\ln P_0)$, and Z=$\nabla \cdot \nabla P_0(2+\ln P_0)$.

* * * * *